US010583090B2

(12) United States Patent
Kaplan et al.

(10) Patent No.: US 10,583,090 B2
(45) Date of Patent: Mar. 10, 2020

(54) VORTEX-INDUCED SILK FIBROIN GELATION FOR ENCAPSULATION AND DELIVERY

(71) Applicant: Trustees of Tufts College, Medford, MA (US)

(72) Inventors: David L. Kaplan, Concord, MA (US); Tuna Yucel, Medford, MA (US)

(73) Assignee: Trustees of Tufts College, Medford, MA (US)

(*) Notice: Subject to any disclaimer, the term of this patent is extended or adjusted under 35 U.S.C. 154(b) by 130 days.

(21) Appl. No.: 15/043,390

(22) Filed: Feb. 12, 2016

(65) Prior Publication Data

US 2016/0263046 A1 Sep. 15, 2016

Related U.S. Application Data

(63) Continuation of application No. 13/320,036, filed as application No. PCT/US2010/036841 on Jun. 1, 2010, now abandoned.

(60) Provisional application No. 61/182,794, filed on Jun. 1, 2009, provisional application No. 61/219,952, filed on Jun. 24, 2009.

(51) Int. Cl.
*A61K 9/50* (2006.01)
*A61K 9/00* (2006.01)
*A61K 47/42* (2017.01)
*A61K 9/06* (2006.01)
*A61K 38/00* (2006.01)

(52) U.S. Cl.
CPC .......... *A61K 9/5052* (2013.01); *A61K 9/0024* (2013.01); *A61K 9/06* (2013.01); *A61K 9/5089* (2013.01); *A61K 47/42* (2013.01); *A61K 38/00* (2013.01)

(58) Field of Classification Search
CPC ......... C08L 89/00; A61K 47/42; A61K 8/042; A61L 27/26; A61L 2400/06; A61L 27/52; A61L 31/046; C08J 2205/022; C07K 14/43586
See application file for complete search history.

(56) References Cited

U.S. PATENT DOCUMENTS

| | | | |
|---|---|---|---|
| 5,245,012 A | 9/1993 | Lombari et al. | |
| 5,589,167 A | 12/1996 | Cleland et al. | |
| 7,635,755 B2 | 12/2009 | Kaplan et al. | |
| 7,674,882 B2 | 3/2010 | Kaplan et al. | |
| 7,842,780 B2 | 11/2010 | Kaplan et al. | |
| 8,178,656 B2 | 5/2012 | Kaplan et al. | |
| 8,206,774 B2 | 6/2012 | Kaplan et al. | |
| 8,293,486 B2 | 10/2012 | Kaplan et al. | |
| 9,016,875 B2 | 4/2015 | Omenetto et al. | |
| 2004/0266992 A1 | 12/2004 | Migliaresi et al. | |
| 2007/0187862 A1* | 8/2007 | Kaplan | A61L 27/227 264/172.11 |
| 2007/0212730 A1 | 9/2007 | Vepari et al. | |
| 2008/0280360 A1 | 11/2008 | Kaplan et al. | |

FOREIGN PATENT DOCUMENTS

| | | |
|---|---|---|
| EP | 0025993 A1 | 4/1981 |
| JP | 11-026344 | 1/1999 |
| WO | WO-97/08315 A1 | 3/1997 |
| WO | WO-04/000915 A2 | 12/2003 |
| WO | WO-04/062697 A2 | 7/2004 |
| WO | WO-2005/012606 A2 | 2/2005 |
| WO | WO-2006/076711 A2 | 7/2006 |
| WO | WO-2007/103442 A1 | 9/2007 |
| WO | WO-2008/106485 A2 | 9/2008 |
| WO | WO-2008/118133 A2 | 10/2008 |
| WO | WO-2008/127401 A2 | 10/2008 |
| WO | WO-2008/150861 A1 | 12/2008 |
| WO | WO-2009/061823 A1 | 5/2009 |
| WO | WO-2009/140588 A1 | 11/2009 |
| WO | WO-2010/036992 A2 | 4/2010 |
| WO | WO-2010/040129 A2 | 4/2010 |
| WO | WO-2010/042798 A2 | 4/2010 |
| WO | WO-2010/057142 A2 | 5/2010 |
| WO | WO-2010/141133 | 12/2010 |
| WO | WO-2011/006133 A2 | 1/2011 |

OTHER PUBLICATIONS

Li et al. The natural silk spinning process. Eur. J. Biochem. 2001;268:6600-6606.*
Altman, G.H. et al., Silk-based biomaterials, Biomaterials, 24(3):401-416 (2003).
Anseth, K.S. et al., In situ forming degradable networks and their application in tissue engineering and drug delivery, Journal of Controlled Release, 78:199-209 (2001).
Bini, E. et al., Mapping domain structures in silks from insects and spiders related to protein assembly, Journal of Molecular Biology, 335(1):27-40 (2004).

(Continued)

*Primary Examiner* — Lynn Y Fan

(74) *Attorney, Agent, or Firm* — Quarles & Brady, LLP

(57) ABSTRACT

The present invention provided for a novel process of forming silk fibroin gels, and controlling the rate of β-sheet formation and resulting hydrogelation kinetics, by vortex treatment of silk fibroin solution. In addition, the vortex treatment of the present invention provides a silk fibroin gel that may be reversibly shear-thinned, enabling the use of these approach for precise control of silk self-assembly, both spatially and temporally. Active agents, including biological materials, viable cells or therapeutic agents, can be encapsulated in the hydrogels formed from the processes, and be used as delivery vehicles. Hence, the present invention provide for methods for silk fibroin gelation that are useful for biotechnological applications such as encapsulation and delivery of active agents, cells, and bioactive molecules.

9 Claims, 15 Drawing Sheets

(56) References Cited

OTHER PUBLICATIONS

Cadix, A. et al., Control of the Reversible Shear-Induced Gelation of Amphiphilic Polymers through Their Chemical Structure, Macromolecules, 38:527-536 (2005).
Chen, X. et al., Rheological Characterization of Nephila Spidroin Solution, Biomacromolecules, 3:644-648 (2002).
Dicko, C. et al., Spider silk protein refolding is controlled by changing pH 5 Biomacromolecules, 5(3):704-710 (2004).
Drury, J.L. and Mooney, D.J., Hydrogels for tissue engineering: scaffold design variables and applications, Biomaterials, 24(24):4337-4351 (2003).
Fini, M. et al., The healing of confined critical size cancellous defects in the presence of silk fibroin hydrogel, Biomaterials, 26(17):3527-2536 (2005).
Haines-Butterick, L. et al., Controlling hydrogelation kinetics by peptide design for three-dimensional encapsulation and injectable delivery of cells, Proceedings of the National Academy of Science USA, 104(19):7791-96 (2007).
Hino, T. et al., Change in secondary structure of silk fibroin during preparation of its microspheres by spray-drying and exposure to humid atmosphere, Journal of Colloid and Interface Science, 266(1):68-73 (2003).
Horan, R.L. et al., In vitro degradation of silk fibroin, Biomaterials, 26(17):3385-3393 (2005).
Inoue, S. et al., Silk fibroin of Bombyx mori is secreted, assembling a high molecular mass elementary unit consisting of H-chain, L-chain, and P25, with a 6:6:1 molar ratio, Journal of Biological Chemistry, 245(51):40517-40518 (2000).
International Search Report and Written Opinion, corresponding to International Patent Application No. PCT/US12/37973 (dated Jul. 30, 2012).
Ishida, M. et al., Solvent- and Mechanical-Treatment-Induced Conformation Transition of Silk Fibroins Studied by High-Resolution Solid-State C NMR Spectroscopy, Macromolecules, 23:88-94 (1990).
Jin, H.J. and Kaplan, D.L., Mechanism of silk processing in insects and spiders, Nature, 424(6952):1057-1061 (2003).
Jin, H.J. et al., Biomaterial films of Bombyx mori silk fibroin with poly(ethylene oxide), Biomacromolecules, 5(3):711-717 (2004).
Jin, H.J. et al., Electrospinning Bombyx mori silk with poly(ethylene oxide), Biomacromolecules, 3(6):1233-1239 (2002).
Kim, U.J. et al., Structure and properties of silk hydrogels, Biomacromolecules, 5(3):786-92 (2004).
Kim, U.J. et al., Three-dimensional aqueous-derived biomaterial scaffolds from silk fibroin, Biomaterials, 26(15):2775-85 (2005).
Langer, R., Biomaterials in drug delivery and tissue engineering: one laboratory's experience, Accounts of Chemical Research, 33(2):94-101 (2000).
Lee, K.Y. and Mooney, D.J., Hydrogels for tissue engineering, Chemical Reviews, 101(7):1869-1879 (2001).
Li, G. et al., The natural silk spinning process, European Journal of Biochemistry, 268:6600-6606 (2001).
Lucas, F. et al., The silk fibroins, Advances in Protein Chemistry, 13:107-242 (1958).
Lutolf, M.P. and Hubbell, J.A. et al., Synthetic biomaterials as instructive extracellular microenvironments for morphogenesis in tissue engineering, Nature Biotechnology, 23(1):47-55 (2005).

MacKintosh, F.C. et al., Elasticity of semiflexible biopolymer networks, Physical Review Letters 75(24):4425-28 (1995).
Matsumoto, A. et al., Mechanisms of Silk Fibroin Sol-Gel Transitions, Journal of Physical Chemistry B, 110:21630-21638 (2006).
Matsumoto, A., et al., Mechanisms of silk fibroin sol-gel transitions, Journal of Physical Chemistry B, 110(43): 21630-21638 (2006).
Matsumoto, K. and Uejima, H., Regenerated Protein Fibers. I. Research and Development of a Novel Solvent for Silk Fibroin, Journal of Polymer Science Part A Polymer Chemistry, 35:1949-1954 (1997).
Matsumoto, K. et al., Regenerated Protein Fibers. II. Viscoeslastic Behavious of Silk Fibroin Solutions, Journal of Polymer Science Part A Polymer Chemistry, 35:1955-1959 (1997).
Nazarov, R. et al., Porous 3-D scaffolds from regenerated silk fbroin, Biomacromolecules, 5(3):718-726 (2004).
Ochi, A. et al., Rheology and dynamic light scattering of silk fibroin solution extracted from the middle division of *Bombyx mori* silkworm, Biomacromolecules, 3(6):1187-1196 (2002).
Onuki, J., Phase transitions of fluids in shear flow, Journal of Physics: Condensed Matter, 9:6119-57 (1997).
Pochan, D.J. et al., Thermally reversible hydrogels via intramolecular folding and consequent self-assembly of a de novo designed peptide, Journal of the American Chemical Society, 125(39):11802-11803 (2003).
Raghu, A. et al., Microrheological studies of regenerated silk fibroin solution by video microscopy, Journal of Polymer Science Part B: Polymer Physics, 45(18):2555-2562 (2007).
Schneider, J.P. et al., Responsive Hydrogels from the Intramolecular Folding and Self-Assembly of a Designed Peptide, Journal of the American Chemical Society, 124:15030-15037 (2002).
Sofia, S. et al., Functionalized silk-based biomaterials for bone formation, Journal of Biomedical Materials Research, 54(1):139-148 (2001).
Terry, A.E. et al., pH induced changes in the rheology of silk fibroin solution from the middle division of *Bombyx mori* silkworm, Biomacromolecules, 5(3):768-772 (2004).
Vollrath, F. and Knight, D.P., Liquid crystalline spinning of spider silk, Nature, 410:541-548 (2001).
Wang, et al., Sonification-induced Gelation of Silk Fibroin for Cell Encapsulation, Biomaterials, 29(8):1054-1064 (2008).
Wang, H. et al., A study on the flow stability of regenerated silk fbroin aqueous solution, International Journal of Biological Macromolecules, 36(1-2):66-70 (2005).
Wang, X. et al., Silk microspheres for encapsulation and controlled release, Journal of Controlled Release, 117(3):360-370 (2007).
Wang, X. et al., Sonication-induced gelation of silk fibroin for cell encapsulation, Biomaterials, 29(8):1054-1064 (2008).
Witten, T.A. and Cohen, M.H., Cross-Linking in Shear-Thickening Ionomers, Macromolecules, 18:1915-1918 (1985).
Yucel, T. et al., Direct Observation of Early-Time Hydrogelation in β-Hairpin Peptide Self-Assembly, Macromolecules, 41(15):5763-5772 (2008).
Zhou, C.Z. et al, Fine organization of Bombyx mori fibroin heavy chain gene, Nucleic Acids Research, 28(12):2413-2419 (2000).
Zhou, L. et al., Effect of metallic ions on silk formation in the Mulberry silkworm, *Bombyx mori*, Journal of Physical Chemistry B 109(35):16937-16945 (2005).

\* cited by examiner

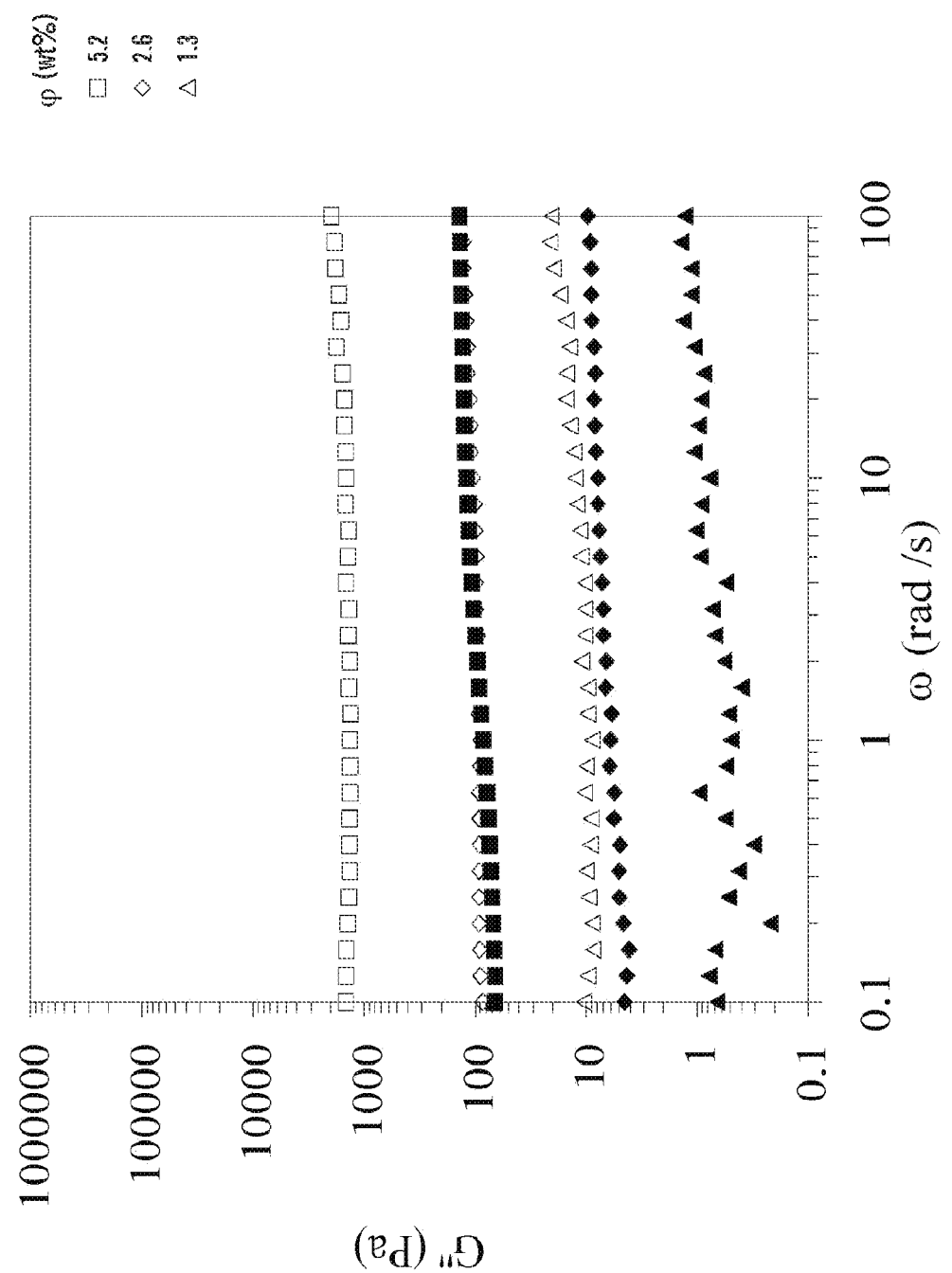

VORTEX-INDUCED SILK FIBROIN GELATION FOR ENCAPSULATION AND DELIVERY

CROSS REFERENCE TO RELATED APPLICATIONS

This application is a continuation of U.S. patent application Ser. No. 13/320,036, filed Dec. 8, 2011, now abandoned, which is the National Stage Application PCT/US2010/36841, filed Jun. 1, 2010 which claims the benefit of priority under 35 U.S.C. § 119(e) of U.S. Provisional Application No. 61/182,794 filed Jun. 1, 2009, and U.S. Provisional Application No. 61/219,952 filed Jun. 24, 2009, the entire contents of each of which are incorporated herein by reference.

GOVERNMENT SUPPORT

This invention was made with government support under grant EB002520 awarded by the National Institutes of Health and grant FA9550-07-1-0079 awarded by the United States Air Force. The government has certain rights in the invention.

FIELD OF THE INVENTION

This invention provides for methods of forming silk fibroin gels comprising vortexing, and methods of delivering active agents encapsulated in vortex-induced silk hydrogels.

BACKGROUND OF THE INVENTION

Biocompatible and biodegradable polymer hydrogels are useful carriers for delivering active agents and cells for biomedical applications, such as in tissue engineering and controlled drug release. Purified native silk fibroin protein forms β-sheet-rich crosslinked hydrogel structures from aqueous solution, with the mechanics of the process and gel properties influenced by environmental parameters. Traditional gelation methods using aqueous native silk protein solutions, under physiologically relevant conditions, often range from days to weeks for gelation: too slow for the incorporation of cells and labile active agents. High temperature, low pH, or high ionic strength may reduce the gelation time to a few hours, but these conditions may potentially alter cell or bioactive molecule function and limit cell viability. Moreover, biological and some physical properties of silk hydrogel scaffolds are crucial for cell encapsulation/delivery applications. For example, hydrogelation kinetics should be controlled to enable homogeneous 3-dimensional (3-D) encapsulation of cells/active agents and prevention of cell/active agent sedimentation. The ease of application of hydrogel/active molecules scaffolds into the target cite with high spatial precision is also of practical consideration for encapsulation/delivery applications. Thus, there remains need in the art for a process of initiating silk fibroin gelation at mild physiological conditions, with controllable kinetics and properties of the silk hydrogel, as well as the delivery of the gels with spatial precision.

SUMMARY OF THE INVENTION

The present invention provides for methods of inducing silk fibroin gelation and forming silk fibroin gels. The method comprises vortexing a silk fibroin solution for a sufficient period of time to initiate intermolecular self-assembly of silk fibroin β-sheet structure. For example, under particular conditions, substantial silk fibroin gelation occurs within 16 hours of the vortex treatment.

Some embodiments of the invention provide for methods of controlling the gelation time of silk fibroin initiated by vortexing a silk fibroin solution for a sufficient period of time to initiate gelation. For example, the gelation time may be controlled by adjusting the time period of the vortex treatment, the concentration of the silk fibroin in solution, or the temperature of the silk fibroin solution after the vortex treatment.

Another embodiment provides for methods of embedding or encapsulating at least one active agent in a silk fibroin hydrogel. The method comprises vortexing a silk fibroin solution for a sufficient period of time to initiate gelation, introducing the agent(s) to the silk fibroin solution before substantial gelation occurs in the silk fibroin solution, and allowing the silk-fibroin to complete gelation to form a silk fibroin gel-embedded active agent. The active agent may be a therapeutic agent, such as a small molecule or drug, or biological materials such as cells.

The present invention also provides for methods of preparing reversible shear-thinning silk fibroin gels. For example, after vortexing a silk fibroin solution for a sufficient period to initiate gelation of the silk fibroin and allowing substantial gelation, the silk gel may be subjected to shear force (e.g., forced through a needle) to induce reversible thinning. Thus, the present invention also provides for a silk gel that may be reversibly shear-thinned.

Some embodiments of the invention relate to methods of delivering a reversibly shear-thinned silk fibroin gel to a target site. One method comprises vortexing a silk fibroin solution for a sufficient period of time to initiate gelation, allowing substantial gelation to occur after the vortex treatment to form a silk fibroin gel, introducing the silk fibroin gel through a shear-inducing delivery device to the target site while applying a shear force to shear-thin the silk fibroin gel, and removing the shear force, whereupon the shear-thinned silk fibroin gel recovers from shear-thinning and re-gels.

Another embodiment of the invention also relates to a method of embedding active agents in a reversible shear-thinned silk fibroin gel, and delivering the reversibly shear-thinned silk fibroin gel-encapsulated active agent to a target site. For example, one method comprises vortexing a silk fibroin solution for a sufficient period of time to initiate gelation, introducing at least one active agent to the silk fibroin solution before substantial gelation occurs in the silk fibroin solution, thereby forming a silk fibroin gel-embedded active agent that may be shear-thinned reversibly, introducing to the target site the active agent-encapsulated silk fibroin gel through a shear-inducing delivery device to the target site while applying a shear force to shear-thin the agent-embedded silk fibroin gel, and removing the shear force, whereupon the shear-thinned silk fibroin gel-embedded active agent recovers gel form.

BRIEF DESCRIPTION OF THE DRAWINGS

FIG. 1A shows far-UV Circular Dichroism (CD) spectra collected immediately after vortexing silk solutions for different durations, $t_v$. FIG. 1B demonstrates correlation between the time evolution of the increase in $[\theta]_{216}$ measured by CD and the shear storage modulus, G' measured by dynamic oscillatory rheology during post-vortex incubation. FIGS. 1C and 1D depict rheology frequency sweeps of storage (FIG. 1C) and loss (FIG. 1D) modulus as a function of post-vortex assembly time, with $t_a$ under the same assembly conditions as in (FIG. 1D). The frequency sweep data collected from non-vortexed silk solution was also given in (FIG. 1C) and (FIG. 1D) for comparison (+).

FIGS. 3C and 3D show frequency sweeps collected from the hydrogels before (open symbols) and immediately after shear-thinning by injection through a 21 gauge needle (closed symbols).

DETAILED DESCRIPTION

Figure 1A:
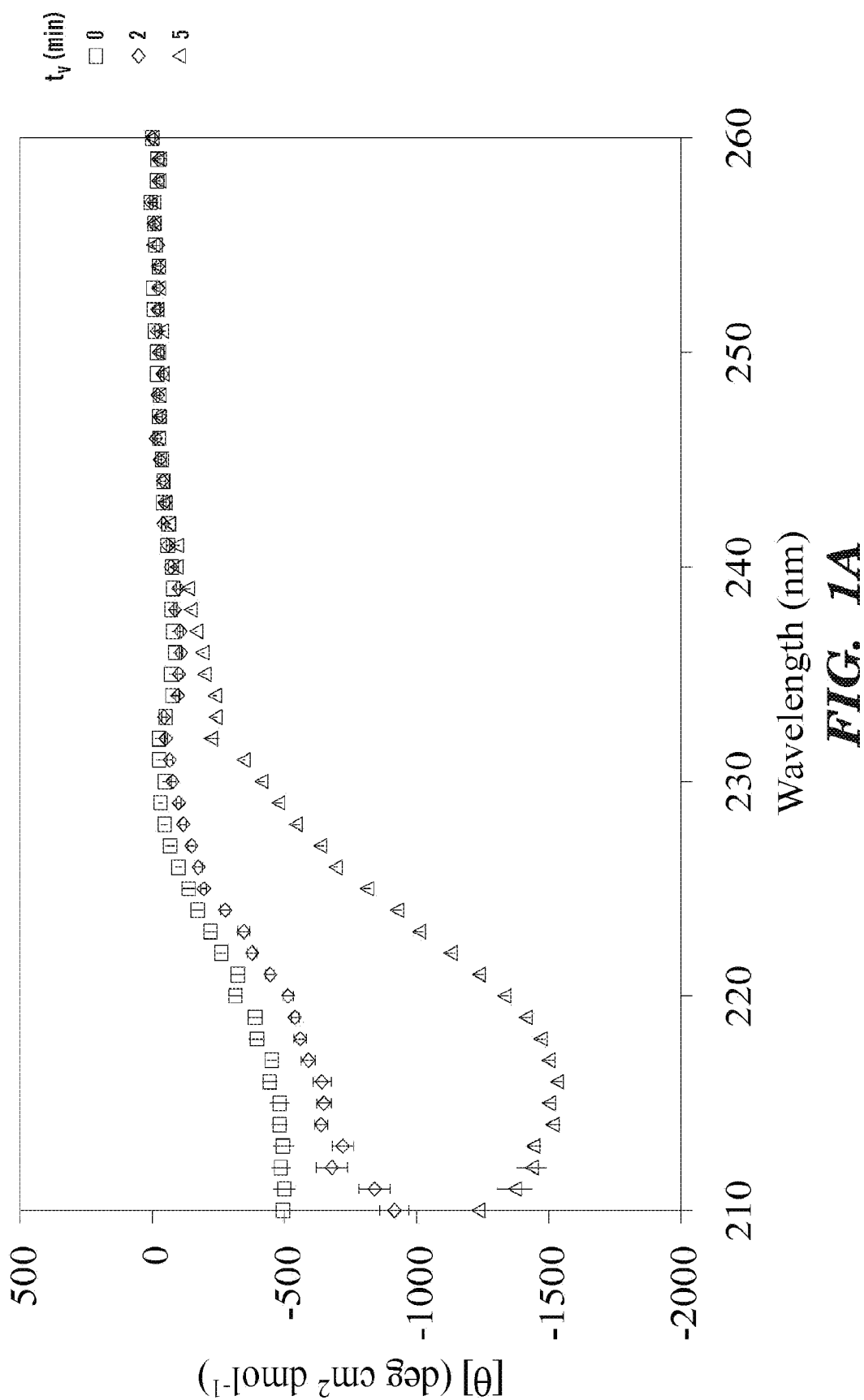
FIGS. 1A-1D depict the dynamic silk fibroin β-sheet structure formation during the gelation process.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

In the present invention, a vortexing technique that causes shear gradient is used to induce changes in silk fibroin structure and solution viscoelastic properties to control the post-vortex self-assembly and hydrogelation kinetics of silk fibroin. The process exposes silk fibroin solution to a treatment comprising vortexing for a sufficient period of time to initiate gelation. Gelation time can be controlled within physiological relevant conditions, ranging from minutes to hours, based on the process parameters used; such as the duration time of vortexing, silk fibroin concentration, and post-vortex assembly temperature of silk fibroin. After vortexing, the silk fibroin undergoes a rapid structural change from random coil to β-sheet, corresponding to gelation. The vortexing technique of the present invention is also used to prepare silk fibroin gels that may be shear-thinned. After the applied shear force is removed, the shear-thinned silk fibroin recovers from shear-thinning and reforms a hydrogel. A active agent, such as for example a therapeutic agent, a biological agent, cells, or the combination of these, can be added to the silk. The present invention thus provides methods for various biomedical applications, such as encapsulation/delivery of cells and bioactive molecules. For example, a shear-thinning hydrogel material could be implanted by minimal invasion to the delivery site, such as by injection through a needle, and such material would recover immediately to a stiff network after removal of applied shear, facilitating localization of a uniform density of cells/bioactive molecules at the delivery site.

Hydrogel materials, both synthetic and natural, are considered useful scaffolds for encapsulation and delivery of cells and active agents, such as for tissue engineering (Lee et al., 101 J. Chemical Reviews 1869-79. (2001)), drug/growth factor release (Langer, 33 Acc. Chem. Res. 94-101 (2000)), and cell therapeutic applications. Hydrogels used in these types of applications have mechanical and structural properties similar to some tissues and extracellular matrices (ECM); therefore, they can be implanted for tissue restoration or local release of therapeutic factors. To encapsulate and deliver cells, hydrogels should, preferably, be formed without damaging cells, be nontoxic to the cells and the surrounding tissue, be biocompatible, have suitable mass transport capability to allow diffusion of nutrients and metabolites, have sufficient mechanical integrity and strength to withstand manipulations associated with implantation, have controllable lifetimes, and should maintain gel volume after implantation for a reasonable period of time depending on the application (Drury & Mooney, 24 Biomaterials 4337-51 (2003)).

A variety of synthetic materials, such as poly(ethylene oxide) (PEO), poly(vinyl alcohol) (PVA), poly(acrylic acid) (PAA), poly(propylene fumarate-co-ethylene glycol) (P(PF-co-EG)), and naturally derived materials, such as agarose, alginate, chitosan, collagen, fibrin, gelatin, and hyaluronic acid (HA) have been used to form hydrogels. Gelation occurs when the polymer chains crosslink either chemically or physically into networks, triggered by chemical reagents (e.g., cross-linkers) or physical stimulants (e.g., pH and/or temperature). Hydrogels formed from synthetic polymers offer the benefit of gelation and gel properties that are controllable and reproducible, through the use of specific molecular weights, block structures, and crosslinking modes.

Synthetic hydrogelating systems can be classified into polymer-based hydrogels (Anseth et al., 10TH INTL. SYMP. RECENT ADV. DRUG DELIV. SYS. 199-209 (Elsevier Sci. By, Salt Lake City, Utah, 2001)), polymer-peptide hybrid hydrogels (Lutolf et al., 23 Natl. Biotechnol. 47-55 (2005)), and peptidic self-assembling hydrogels (Pochan et al., 125 J. Am. Chem. Soc. 11802-03 (2003); Schneider et al., 124 J. Am. Chem. Soc. 15030-37 (2002)). Peptidic hydrogel systems are promising synthetic materials because they generally show low immunogenicity and controllable assembly kinetics, nanostructure formation and hydrogel mechanical properties (Haines-Butterick et al., 104 P.N.A.S. 7791-96 (2007); Yucel et al., 41 Macromolecules 5763-72 (2008)).

Additionally, natural biopolymeric systems generally show better compatibility for hosting cells and bioactive molecules (Lutolf et al., 23 Natl. Biotechnol. 4755 (2005)). Among naturally derived biomaterials, silk fibroin protein, the self-assembling structural protein in natural silkworm fibers, has been studied because of its excellent mechanical properties, biocompatibility, controllable degradation rates, and self assembly into β-sheet rich networks (Altman et al., 24 Biomats. 401-16 (2003); Horan et al., 26 Biomats. 3385-93 (2005); Ishida et al., 23 Macromolecules 88-94 (1990); Jin et al., 424 Nature, 1057-61 (2003); Kim et al. 26 Biomats. 2775-85 (2005)). Silk fibroin hydrogels are of interest for many biomedical applications, such as bone-filling materials (Fini et al., 26 Biomats. 3527-36 (2005)), and cell encapsulation for 3-D cell culture (Wang et al., 29 Biomats. 1054-64 (2008)).

Silk fibroin is a high-molecular weight block copolymer consisting of a heavy (~370 kDa) and a light chain (~26 kDa) with varying amphiphilicity linked by a single disulfide bond (Inoue et al., 275 J. Biol. Chem. 40517-18 (2000)). The heavy chain contains hydrophobic, repetitive oligopeptides rich in alanine and glycine amino acids interspersed with small, more hydrophilic, charged and amorphous regions that give the chain a polyelectrolyte nature. The sequence of the light chain is less repetitive and has a high content of glutamic and aspartic acid residues. Silk fibroin has been processed into a variety of material formats, such as films, electrospun fibers, 3-D porous scaffolds, microspheres and hydrogels, mainly for tissue engineering and cell/drug delivery applications (Kim et al., 5 Biomacromol. 786-92 (2004); Matsumoto et al., 110 J. Phys. Chem. B 21630-38 (2006); Wang et al., 36 Intl. J. Biol. Macromol. 66-70 (2005); Wang et al., 29 Biomats. 1054-64 (2008); Hino et al., 266 J. Colloid & Interf. Sci. 68-73 (2003); Jin et al., 3 Biomacromol. 1233-39 (2002); Jin et al., 5 Biomacromol. 711-17 (2004); Nazarov et al., 5 Biomacromol. 718-26 (2004); Wang et al., 117 J. Control. Release 360-70 (2007)). See also U.S. patent application Ser. No. 11/020,650; Ser. No. 10/541,182; Ser. No. 11/407,373; and Ser. No. 11/664,234; WO/2008/118133; WO/2008/106485.

In nature, silk fibroin aqueous solution is produced in the posterior section of silkworm gland and then stored in the middle section at a high solution concentration and contains a high content of random coil or α-helical structure. The silk fibroin protein goes through a structural transition into β-sheet-containing fibers during fiber spinning into air, due to elongational and shear forces and the concomitant changes in the ionic concentration and pH (Chen et al., 3 Biomacromol. 644-48 (2002); Dicko et al., 5 Biomacromol. 704-10 (2004); Terry et al., 5 Biomacromol. 768-72 (2004); Vollrath et al., 410 Nature 541-48 (2001); Zhou et al., 109 J. Phys. Chem. B 16937-45 (2005)), leading to the formation of solid fibers (Vollrath & Knight, 410 Nature, 541-48 (2001)). In vitro, purified silk fibroin aqueous solutions undergo self-assembly into β-sheet structures and form hydrogels. This sol-gel transition may be influenced by temperature, pH, and ionic strength (Wang et al., 2005; Kim et al., 2004; Matsumoto et al., 2006). For example, the compressive strength and modulus of silk hydrogels increases with an increase in silk fibroin concentration and temperature (Kim et al., 2004).

Both shear and elongation forces have been reported to induce structural transition of silk fibroin into β-sheet containing fibers. In addition, shear forces have also been reported to affect the rheological properties of aqueous silk fibroin solutions. For example, an anomalous shear thickening followed by shear thinning behavior was reported at or above 4.2 wt % silk fibroin concentrations (Ochi et al., 3 Biomacromol. 1187-96 (2002)), similar to that observed for associating polymers (Cadix et al., 38 Macromol. 527-36 (2005); Witten et al., 18 Macromol. 1915-18 (1985)). This behavior was related to the alignment and stretching of polymer chains induced by the shear rate gradient and alternating rupture and recovery of the crosslinks. At higher silk concentrations of about 25 wt %, a phase separation between a white, tough material and the surrounding clear liquid was reported at steady shear rates above 2 $s^{-1}$ (Terry et al., 5 Biomacromol. 768-72 (2004)). This apparent phase separation was attributed to shear-induced crystallization into a β-sheet structure by stretching of fibroin molecules due to the applied flow field and repulsion of bound water at relatively low shear rates as compared to those within the silkworm duct. At higher silk concentrations of about 25 wt %, a phase separation between a white, tough material and the surrounding clear liquid was reported at steady shear rates above 2 $s^{-1}$ (Terry et al., 2004). This apparent phase separation was attributed to shear-induced crystallization into a β-sheet structure by stretching of fibroin molecules due to the applied flow field and repulsion of bound water at relatively low shear rates as compared to those within the silkworm duct.

Silk fibroin hydrogels are of interest for many biomedical applications, such as bone-filling materials (Fini et al., 26 Biomats. 3527-36 (2005)), implantable medical devices, bioactive molecules encapsulation, and cell encapsulation for 3-D cell culture (Wang et al., 2008). See also WO 2008/150861; PCT/US2009/058534.

For many cell-based applications, self-assembly into β-sheet structure and concomitant hydrogelation of silk fibroin must be induced under mild conditions in a relatively short period of time (within hours). Silk gelation is typically too slow under physiologically relevant solution conditions, in the absence of chemical modifications to the native silk fibroin protein, for the realization of cell encapsulation applications. For silk fibroin concentrations from 0.6% to 15% (w/v), days to weeks were required for the sol-gel transition at room temperature or 37° C. (Kim et al., 2004; Matsumoto et al., 2006; Fini et al., 2005). Nonphysiological treatments, such as lowering pH, increasing temperature or increasing high ionic strength may reduce the self-assembly and hydrogelation time of silk fibroin to a few hours (Kim et al., 2004); Matsumoto et al., 2006; Wang et al., 2005), but these conditions both potentially alter cell function and affect cell viability. One way to induce rapid and controlled hydrogelation of the silk fibroin, in the absence of harsh solution conditions, is by ultrasonication treatment (Wang et al. 29 Biomats. 1054-64 (2008)).

Additionally, for cell encapsulation/delivery applications, several biological (e.g., cytocompatibility, cell adhesion and subsequent cell morphological changes, cell proliferation, cell phenotype maintenance, and, in some cases, cell proliferation, and post-injection biodegradability of hydrogel matrix), and some physical (bulk mechanical properties as determined by the local and global structure) properties of hydrogel scaffolds are considered crucial. Other materials criteria should also be met before widespread use of these materials for cell delivery applications (Haines-Butterick et al., 104 P.N.A.S. 7791-96 (2007); Yucel, *Early-Time, β-Hairpin Self-Assembly & Hydrogelation: Structure, Kinetics & Shear-Recovery* (Ph.D. Dissertation, Univ. Delaware, Newark, 2008). For example, hydrogelation kinetics should be controlled precisely to enable homogeneous 3-D encapsulation of cells and prevention of cell sedimentation.

Another practical consideration for injectable hydrogel/cell scaffolds is the ease of application into the body with high spatial precision (Haines-Butterick et al., 2007). For example, a shear-thinning hydrogel material can be implanted by minimal invasion to the delivery site, such as by injection through a needle. Thus, a hydrogel that shear-thins into a sol-state during injection enables a homogeneous delivery of cells to a wound site, as compared with cell delivery in solution. In addition, it may be important for the shear-thinned hydrogel material to recover quickly or immediately into a stiff network after removal of applied shear force, facilitating localization of a uniform density of cells at the delivery site.

In the present invention, novel methods to induce and control the formation of silk fibroin β-sheet structure and the concomitant silk hydrogelation are accomplished through vortex treatment. More specifically, a new vortexing-based method is presented that accelerates the sol-gel transition in a temporally controllable manner. The method comprises vortexing a silk fibroin solution for a sufficient period of time to initiate intermolecular self-assembly of silk fibroin β-sheet structure. For example, under particular conditions, substantial silk fibroin gelation occurs within 16 hours of the vortex treatment. After vortexing, the silk fibroin undergoes a rapid structural change from random coil to β-sheet, corresponding to gelation. Gelation-time can be controlled, ranging from minutes to hours, based on the process parameters used. The methods further provide for manipulation of the duration time of vortexing, silk fibroin concentration, and post-vortex assembly temperature of silk fibroin to affect the formation of silk hydrogelation, the dynamics structural changes after gelation, and physical properties of silk gel.

A broad range of silk fibroin concentrations, in the aqueous solution, are suitable for the vortex treatment in the present invention. For example, the concentration of silk fibroin in solution may be less than about 30 wt %. Typically, lowering the initial silk protein concentration reduces the final hydrogel stiffness and increases the silk gelation time. The vortex treatment of the present invention allows induction of silk fibroin gelation at a lower protein concentration than those studied previously. For example, an aqueous solution having a concentration about 6 wt % fibroin or lower may be used. A particular embodiment is directed towards the use of an aqueous solution having a concentration ranging from about 1 wt % to about 5.2 wt % fibroin. Another embodiment is directed towards the use of an aqueous solution having a concentration of about 1.3 wt % fibroin or lower, for instance, from about 0.3 wt % fibroin to about 1.3 wt % fibroin.

As used herein, the term "fibroin" includes silkworm fibroin and insect or spider silk protein. See e.g., Lucas et al., 13 Adv. Protein Chem. 107-242 (1958). Any type of silk fibroin may be used according to the present invention. Silk fibroin produced by silkworms, such as *Bombyx mori*, is the most common and represents an earth-friendly, renewable resource. For instance, silk fibroin used in a silk gel may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used. An aqueous silk fibroin solution may be prepared from silkworm cocoons using techniques known in the art. Suitable processes for preparing silk fibroin solution are disclosed, for example, in U.S. patent application Ser. No. 11/247,358; WO/2005/012606; and WO/2008/127401.

Vortex treatment is used in the present invention to apply shear-gradient to silk fibroin solution to induce sol-gel transition of silk fibroin and control the post-vortex self-assembly and hydrogelation kinetics. Shear-induced gelation has been reported for polymers in poor solvents (Onuki, 9 J. Phys.-Condens. Matter 6119-57 (1997)), and amphiphilic associating polymers (Cadix et al., 38 Macromol. 527-36 (2005); Witten et al., 18 Macromol. 1915-18 (1985)). For polymers in poor solvents, shear flow is believed to increase the concentration fluctuations, which may lead to the assembly of macromolecules in the absence of excluded volume in a poor solvent (Onuki, 1997). For associating polymers, increased intermolecular interactions between self-associating chains that undergo non-Gaussian stretching due to flow were argued to lead to shear-induced gelation (Witten et al., 18 Macromol. 1915-18 (1985)). The present invention provides for a novel technique for causing shear gradient to induce a sol-gel transition of silk fibroin and control the post-vortex self-assembly and hydrogelation kinetics.

Generally speaking, vortex treatments may be performed in any manner known in the art. A commercially available vortexer may be used for the vortex treatment. The vortex treatment may involve exposing the silk fibroin to vortexing one time, or may involve multiple separate exposures. The vortex treatment should last for a period of time sufficient to initiate the gelation process, but not so long as to compromise the mechanical properties of the hydrogel. Typically, vortex treatments may last from 2 minutes to 15 minutes depending on the rotational speed of the vortexer, the amount of silk fibroin used, the concentration of the solution, and other factors appreciated by those of ordinary skill in the art. For example, the vortex treatments last from about 2 minutes to about 11 minutes.

Figure 1B:
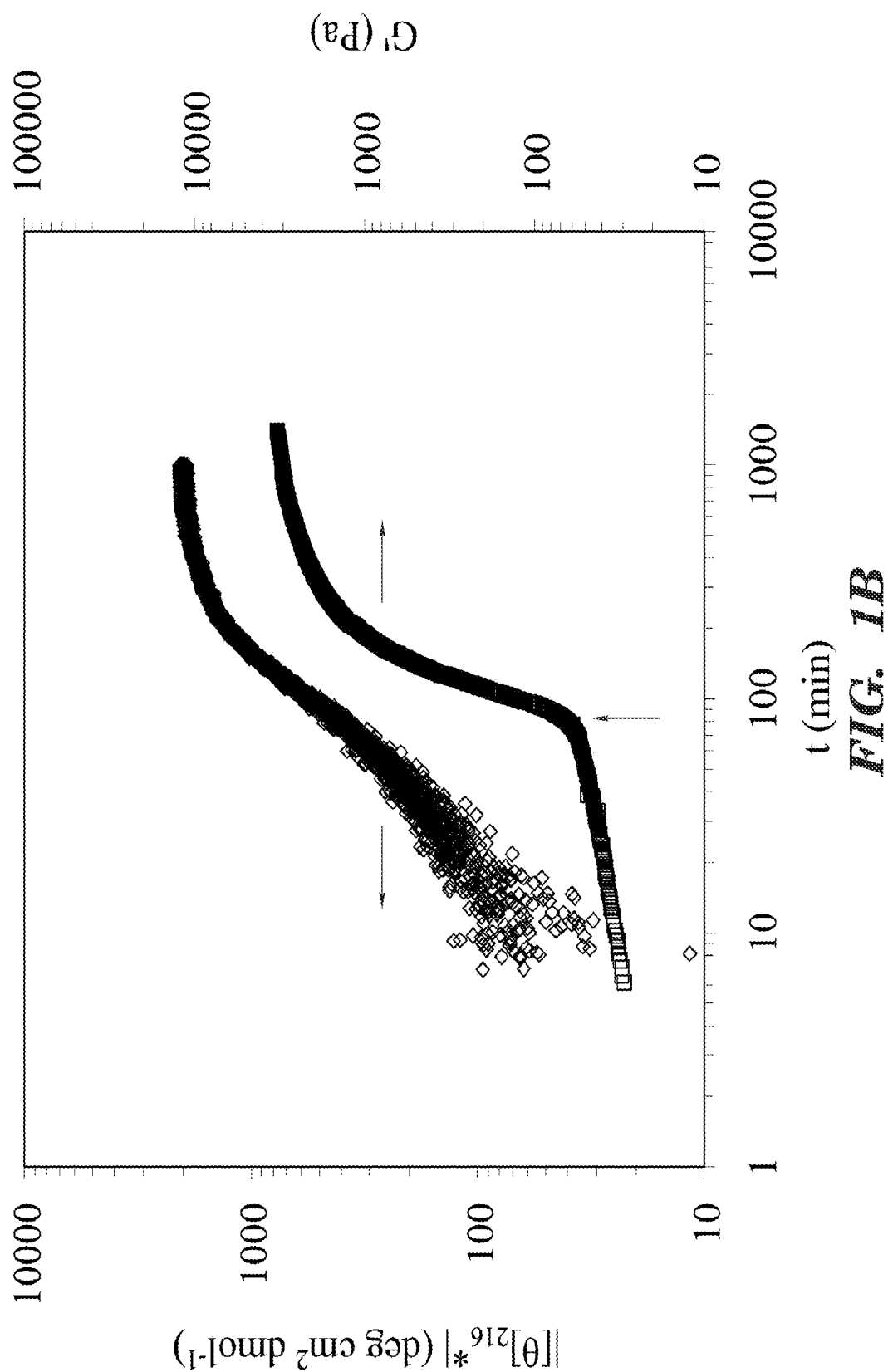

Gelation typically begins at the onset of the vortex treatment and continues after the treatment ends. The vortex treatment initiate structural transition of silk fibroin from random coil and α-helical rich structures into β-sheet structures and form hydrogels. This process is sol-gel transition. The dynamics of gelation of silk fibroin solution may be characterized by measuring the β-sheet content through Circular Dichroism (CD) spectroscopy and dynamic oscillatory rheology under the same assembly conditions at the same time points after triggering hydrogelation by vortexing. This process could capture the isotemporal evolution of the overall protein structure, correlated to concomitant changes in viscoelastic properties, due to vortex-induced hydrogelation. For example, FIG. 1A shows far-UV CD spectra collected from aqueous native silk solutions with a protein concentration $\varphi=1.3$ wt % at 25° C. immediately after vortex treatment. Non-vortexed silk solution did not show any local minima attributable to α-helical or β-sheet conformations within the observed wavelength range (210 nm<λ<260 nm), indicating that the molecular conformation is predominantly random-coil in solution. Vortexing the silk solution for 2 minutes ($t_v=2$ min) lead to a detectable increase in the apparent β-sheet content, as observed by the formation of a local minimum at $\lambda=216$ nm in the CD signal ($[\theta]_{216}$). FIG. 1B shows the dependence of β-sheet content detected by CD spectroscopy and the shear storage modulus, G' measured by dynamic oscillatory rheology on post-vortex assembly time, $t_a$ (25° C., $\varphi=2.6$ wt %, and $t_v=7$ min). Here, $[\theta]_{216}^*$ was calculated by subtracting the $[\theta]_{216}$ value obtained from non-vortexed silk solution rich in random coil content from the $[\theta]_{216}$ value measured from the sample to observe the evolution of β-sheet content due to silk self-assembly.

The time progress of $[\theta]_{216}$* and G' were very similar, showing a gradual increase with increasing assembly time. In a double logarithmic scale, G' initially increased gradually, followed by a rapid increase in G' after $t_a$~100 minutes. This orders of magnitude increase in G' may indicate a percolation-like transition due to increasing connectivity of β-sheet rich macromolecule clusters to form a hydrogel network. Overall, a strong correlation was apparent between the increasing β-sheet content due to changes in molecular conformation and intermolecular self-assembly possibly leading to macromolecular cluster formation and the subsequent increase in the elastic-like behavior, presumably due to increasing intercluster interactions. CD spectroscopy indicates that vortexing aqueous solutions of silkworm silk lead to a transition from an overall protein structure that is initially rich in random coil to that rich in β-sheet content. Dynamic oscillatory rheology experiments collected under the same assembly conditions as the CD experiments indicates that the increase in β-sheet content due to intramolecular conformational changes and intermolecular self-assembly of the silk fibroin was directly correlated with the subsequent changes in viscoelastic properties due to hydrogelation. With increasing vortex time ($t_v$=5 min), the absolute value of $[\theta]_{216}$ increased further, suggesting an increase in the overall β-sheet content.

Formation of a hydrogel with substantial stiffness corresponds to the formation of substantial β-sheet content and the substantial gelation of silk fibroin. For example, samples with an initial protein concentration ≥1.3 wt % (G' ca. 100 Pa) formed self-supporting gels while lower concentration samples apparently flowed after inversion of sample vials. Moreover, the solid-like, opaque phase that formed during vortexing precipitated out during subsequent incubation for protein concentrations lower than 1.3 wt %. Therefore, G' values ≥100 Pa could be considered to represent "substantial hydrogel stiffness" for practical purposes. Substantial gelation usually occurs within 16 hours after the vortex treatment. For example, the silk fibroin gel forms in less than 2 hours after the vortex treatment. In a particular embodiment, the silk fibroin undergoes gelation at a time period ranging from about 5 minutes to about 2 hours after the vortex treatment. Thus, depending on requirements, gelation time can occur from minutes to hours, based on the vortex treatment of the silk fibroin solution. A strictly defined lower threshold for a vortex time may not be obtainable due to the complication of measurements. When the gelation kinetics of silk fibroin solution is characterized by CD spectroscopy, even 1 minute of vortex treatment of 1 mL silk solutions at a vortex speed of 3,200 rpm could result in an apparent increase in the overall β-sheet content. This apparent β-sheet content increase could presumably speed the gelation kinetics compared to non-vortexed solutions. Note that in measuring the stiffness of gelation for practical "substantial hydrogel stiffness," characterized by dynamic oscillatory rheology (e.g., G' of about 100 Pa for 1.3 wt % hydrogels), vortex times less than 5 minutes at 25° C. may not induce gelation fast enough for rheological measurements.

Figure 1C:
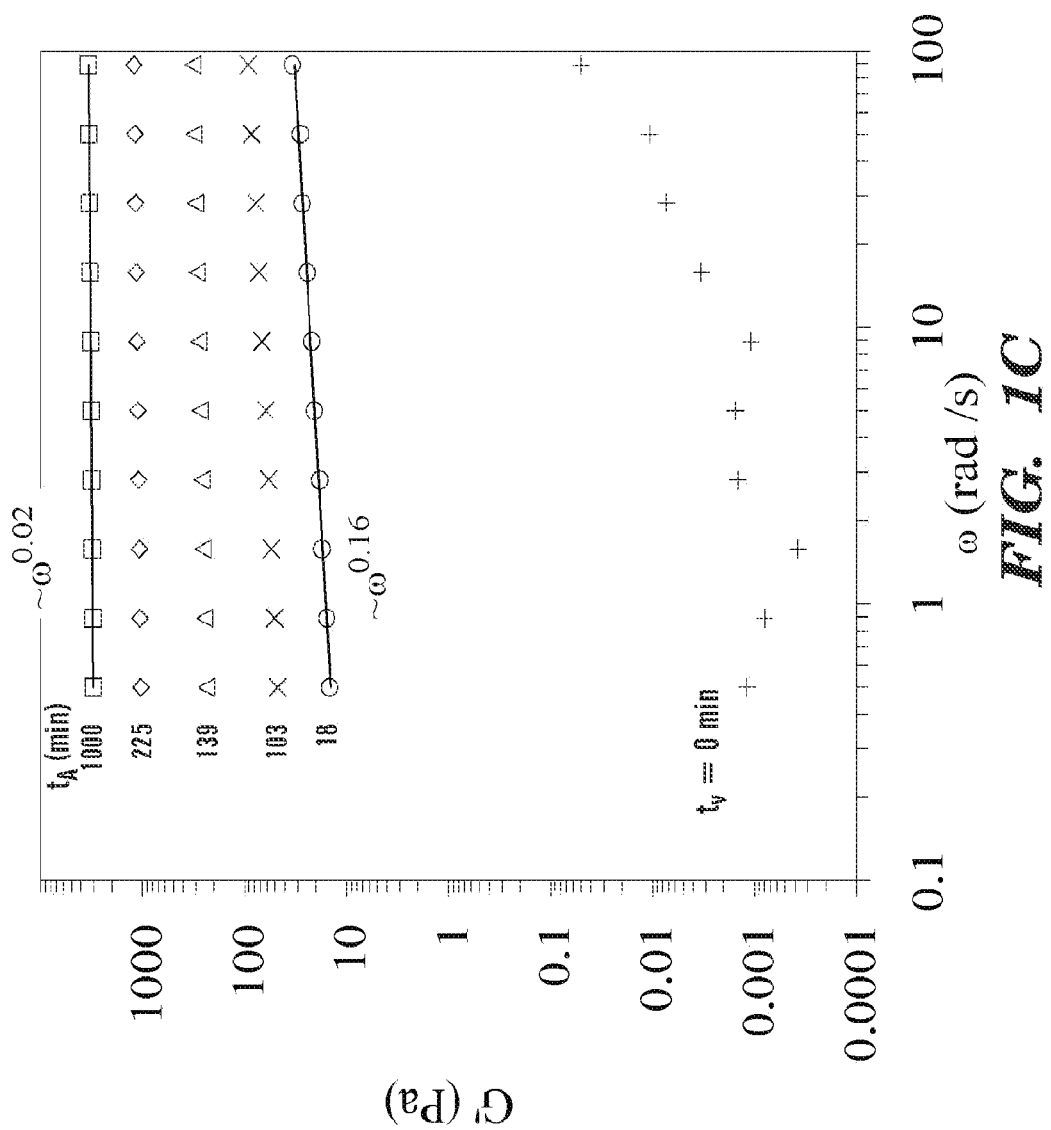
Figure 1D:
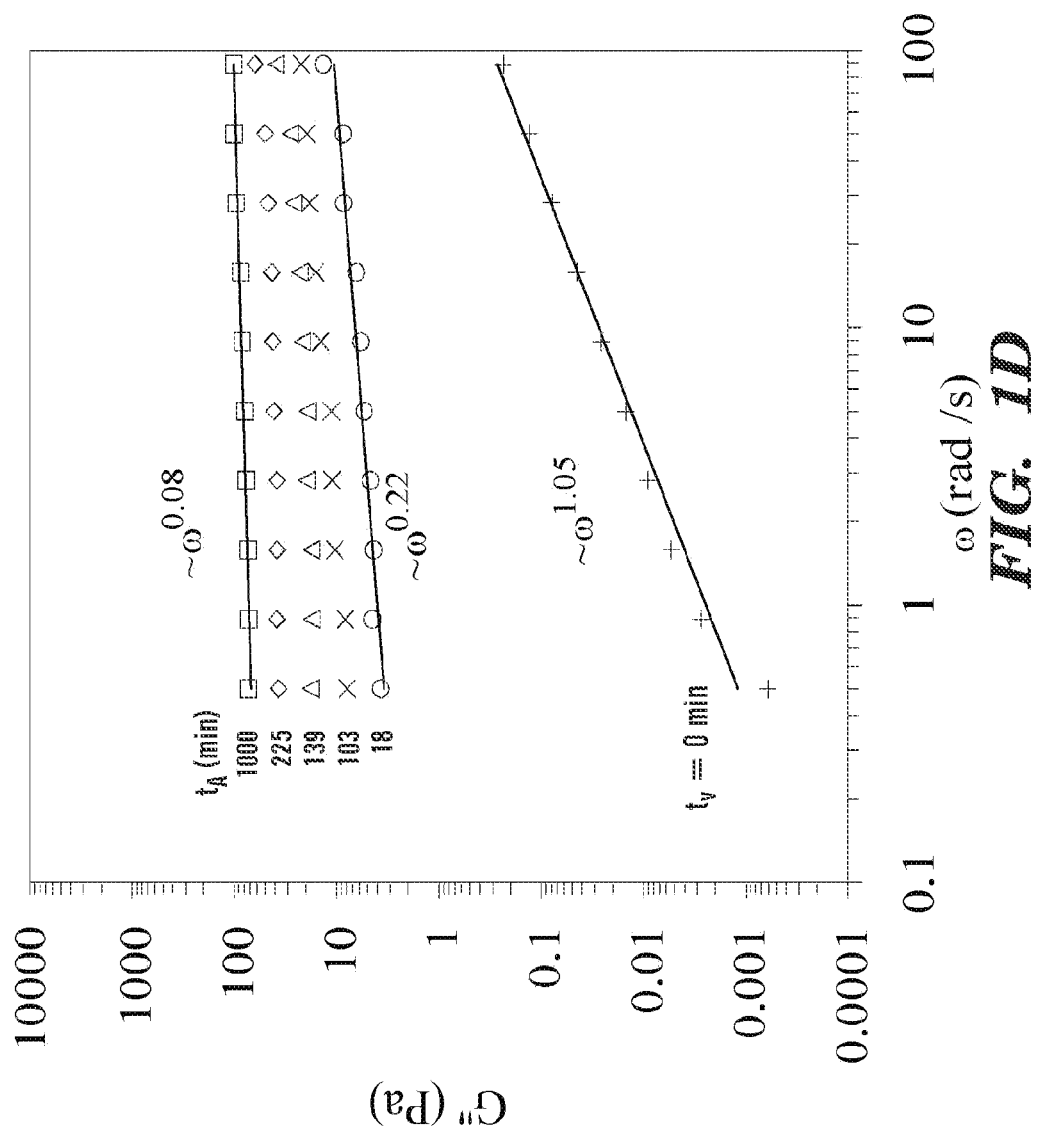

FIGS. 1C and 1D show the time evolution of the dynamic frequency sweeps of the shear storage (G') and loss modulus (G") during post-vortex self-assembly collected under the same assembly conditions as in FIG. 1B. Non-vortexed silk fibroin solution essentially behaved as a low viscosity, Newtonian fluid within the measured frequencies (dynamic complex viscosity, η*~3 mPa·s). There was a significant increase in the elastic-like behavior immediately after vortexing: Both G' and G" increased by orders of magnitude, with G'>G" at all measured frequencies. G' showed a weaker frequency dependence than G" (G' ~$\omega^{0.16}$ and G"~$\omega^{0.22}$), suggesting that the macromolecule clusters could essentially behave as viscoelastic fluids displaying gel-like behavior within the observed frequency range. The apparent gel-like behavior may be attributed to the relatively large size of the micron-scale macromolecule clusters. With increasing assembly time after vortexing, there was a gradual increase in both G' and G" which showed progressively weaker frequency dependence, especially after the apparent percolation transition of the clusters at t~100 minutes. G' and G" became essentially frequency independent within the measured frequency range after $t_a$*~1000 min of assembly (G'~$\omega^{0.02}$ and G"~$\omega^{0.08}$), suggesting the formation of a hydrogel network consisting of permanent intercluster physical crosslinks.

Without being bound by theory, the mechanism of vortex-induced hydrogelation of the silk fibroin may be analogous to shear-gradient induced hydrogelation. Silk fibroin protein is an amphiphilic, block copolymer that consists of segments with predominantly hydrophobic domains that are phase-separated in the nanometer scale to enable solubilization in water (Bini et al., 335 J. Mol. Biol. 27-40 (2004)). Based on overall hydropathy of silk fibroin (in the absence of the nanophase-separated, folded molecular arrangement), water can be considered as a poor solvent for the high molecular weight silk molecules. For example, viscoelastic characterization of silk fibroin solutions in $LiBr.H_2O/H_2O/C_2H_5OH$ mixed solvents showed that the solution dynamic viscosity and flow activation energy decrease with increasing water content, while the dissolution time and the concentration of LiBr necessary to dissolve silk fibroin increased with increasing water content, suggesting that water acts as a poor solvent in this solvent system (Matsumoto & Uejima, 35 J. Polym. Sci. Pol. Chem. 1949-54 (1997); Matsumoto et al., 35 J. Polym. Sci. Pol. Chem. 1955-59 (1997)). The shear-gradient caused by vortex treatment increases the concentration fluctuations in the aqueous silk solution, which could lead to self-assembly of silk fibroin into β-sheet rich silk macromolecule clusters and increased intercluster interactions in the absence of excluded volume. Perhaps the spatial heterogeneity of concentration fluctuations or a shear gradient may be responsible for controlling the kinetics of native silk hydrogelation: The shear-gradient may cause non-Gaussian stretching (unfolding) of silk fibroin molecular domains and formation of macromolecule clusters rich in β-sheet content due to increased exposure of hydrophobic domains to water. Increasing size and concentration of β-sheet macromolecule clusters, and subsequent increase in the concentration and overall lifetime of intercluster crosslinks and the physical entanglements between dangling fibroin chains, could eventually lead a percolation-like transition into a permanent, physical hydrogel network.

The vortex treatment described herein may include other treatment(s) to assist in the gelation process. In one embodiment, increasing the vortex time increases the silk fibroin solution turbidity and may yield a bulk phase separation of a white, solid-like material from the aqueous phase, especially at lower silk fibroin concentrations. The treatment therefore may further comprise removing the solid phase and allow gelation of the remaining aqueous phase. This visible, solid-like, sticky phase may form for all vortex times ($t_v$≥5 min) and silk protein concentrations that provide suitable gelation kinetics. Such solid phase could potentially be useful, for example, for muco-adhesive applications.

As mentioned, the aqueous silk fibroin solution under vortex treatment may have a broad range of concentration. The concentration may be less than about 30 wt %. Typically, lowering initial protein concentration reduces the final hydrogel stiffness and increases the time of silk gelation. The vortex treatment of the present invention allows initiation of silk fibroin gelation at a lower protein concentration than those previously studied. For example, an aqueous solution having a silk fibroin concentration of about 6 wt % or less may be used. A particular aspect is directed towards the use of an aqueous solution having a silk fibroin concentration about 1 wt % or higher.

Figure 2A:
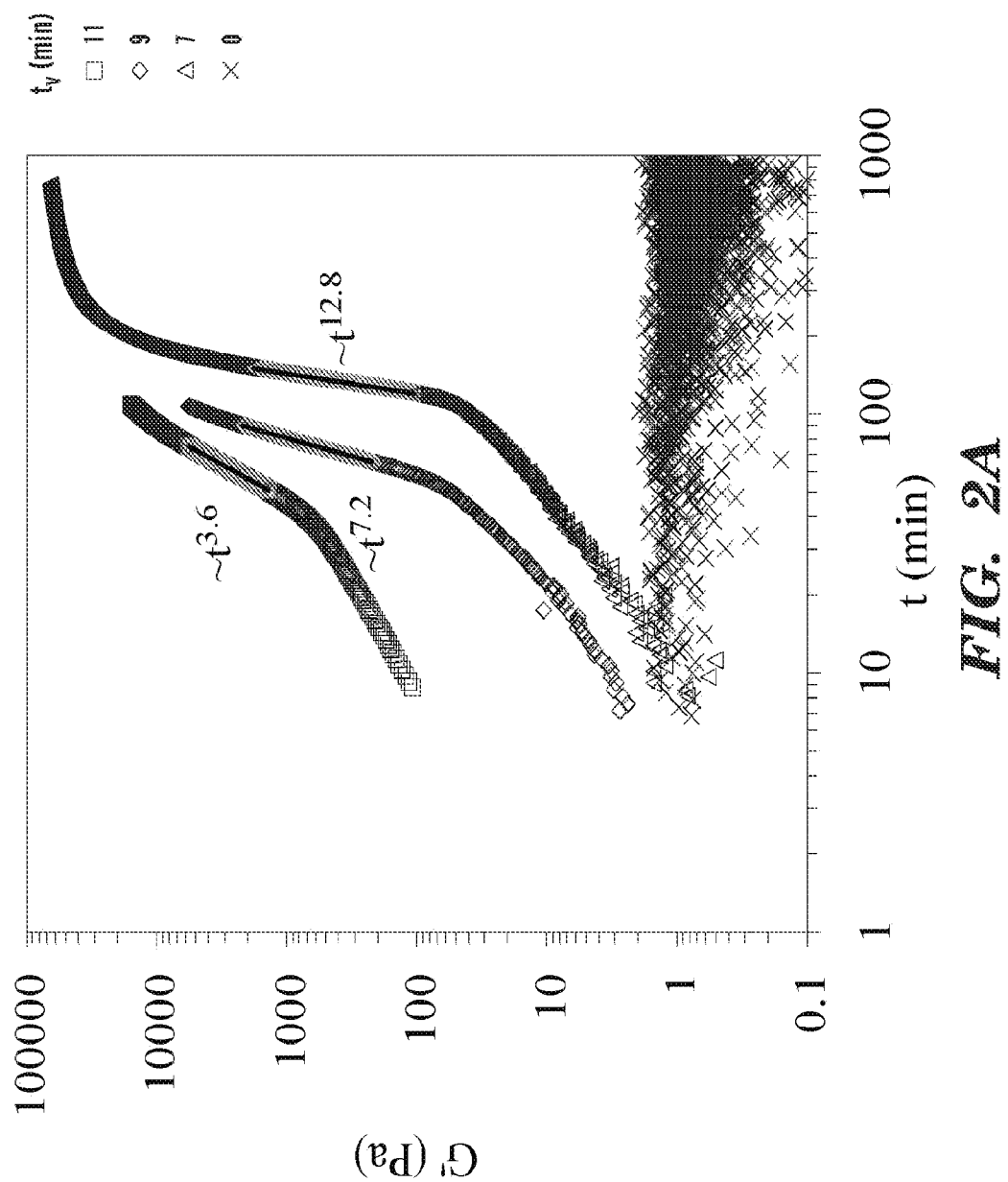
FIGS. 2A-2F depict the kinetics of silk fibroin hydrogelation under various conditions. The kinetics of silk fibroin hydrogelation are examined by varying vortex time (FIGS. 2A and 2B), assembly temperature (FIGS. 2C and 2D) and protein concentration (FIGS. 2E and 2F). Power law exponents in FIG. 2A were obtained from fits to the blue-colored G' data. $t_v$=7 min for (FIGS. 2C-2F).
Figure 2B:
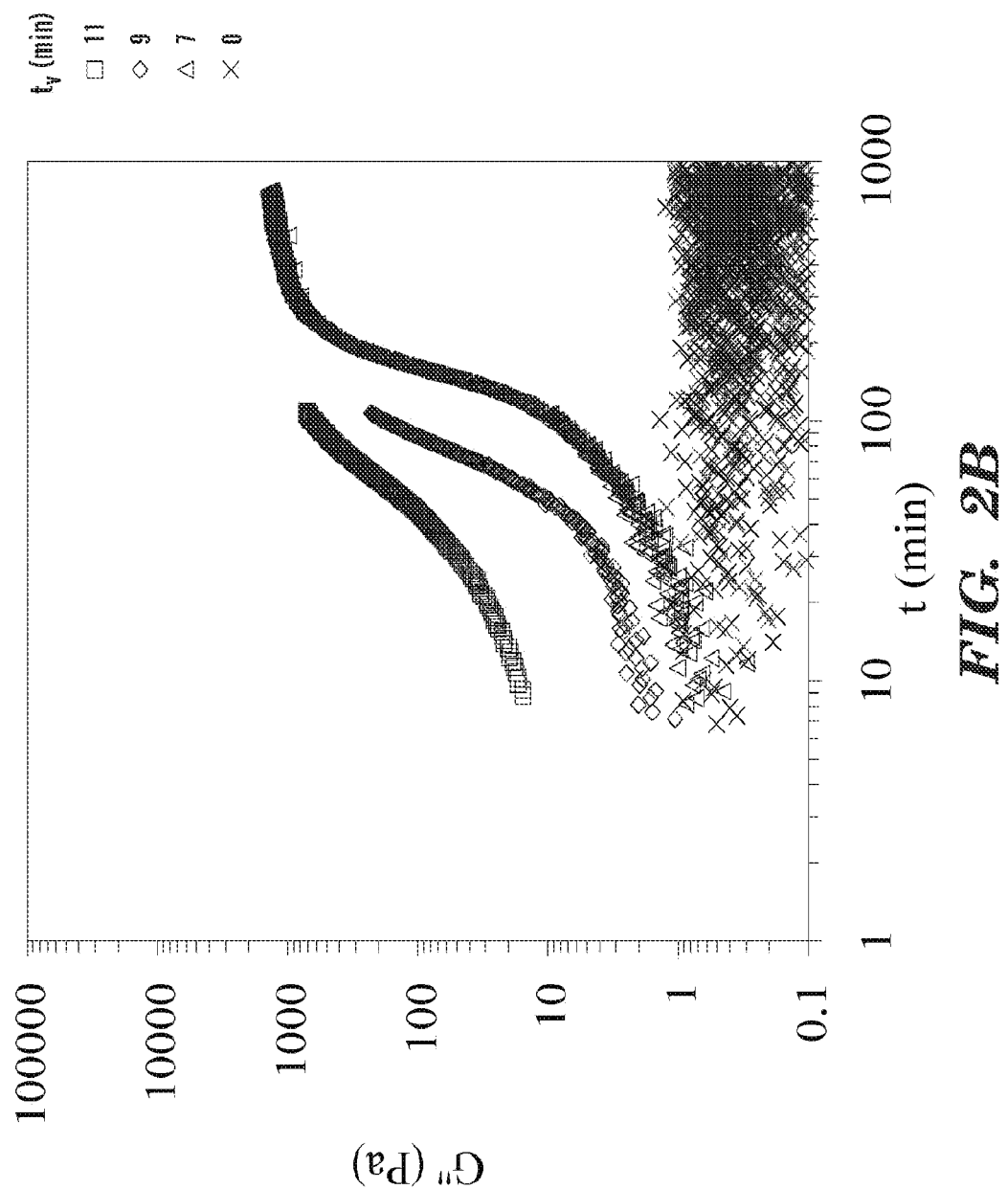
Figure 2C:
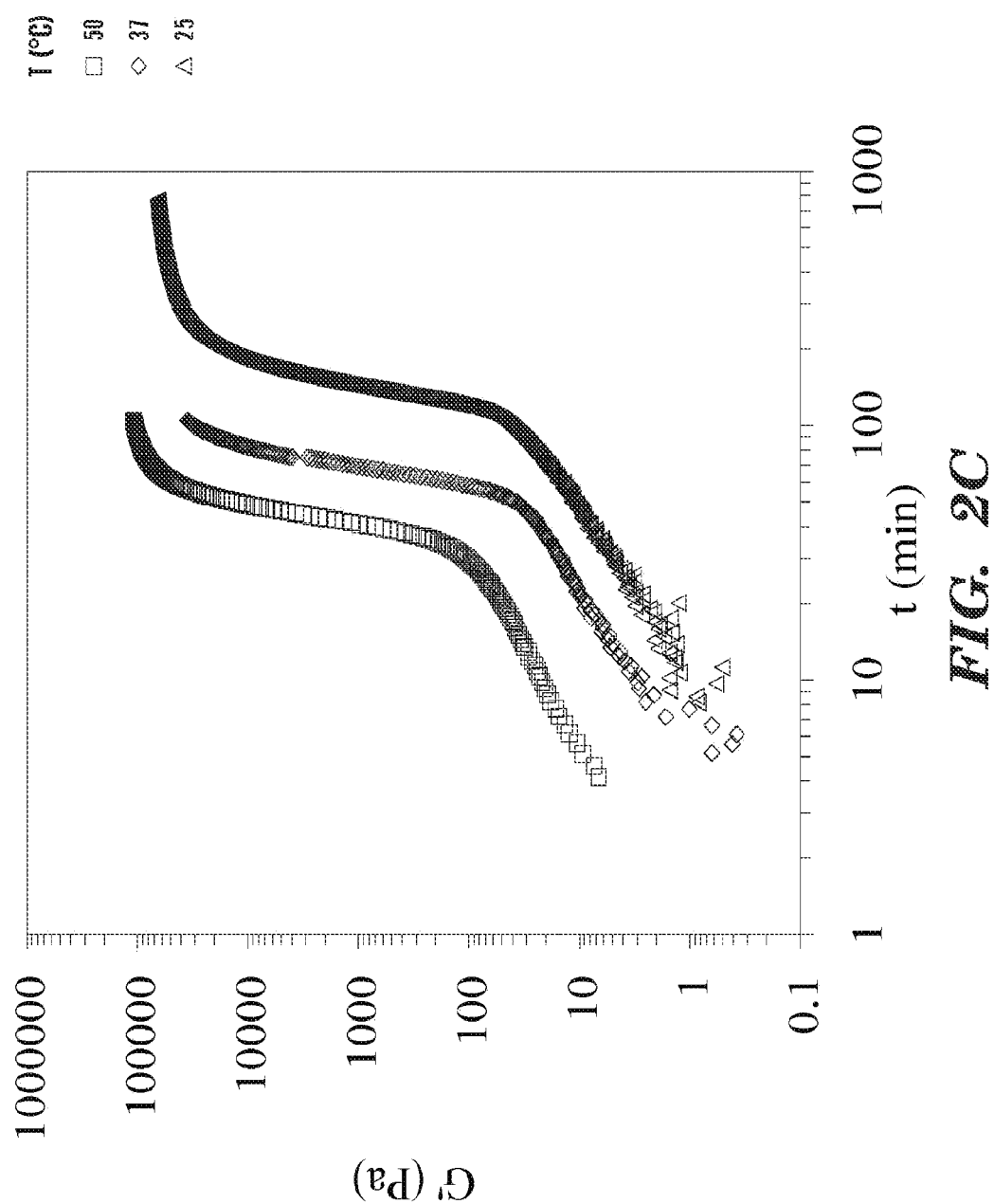
Figure 2D:
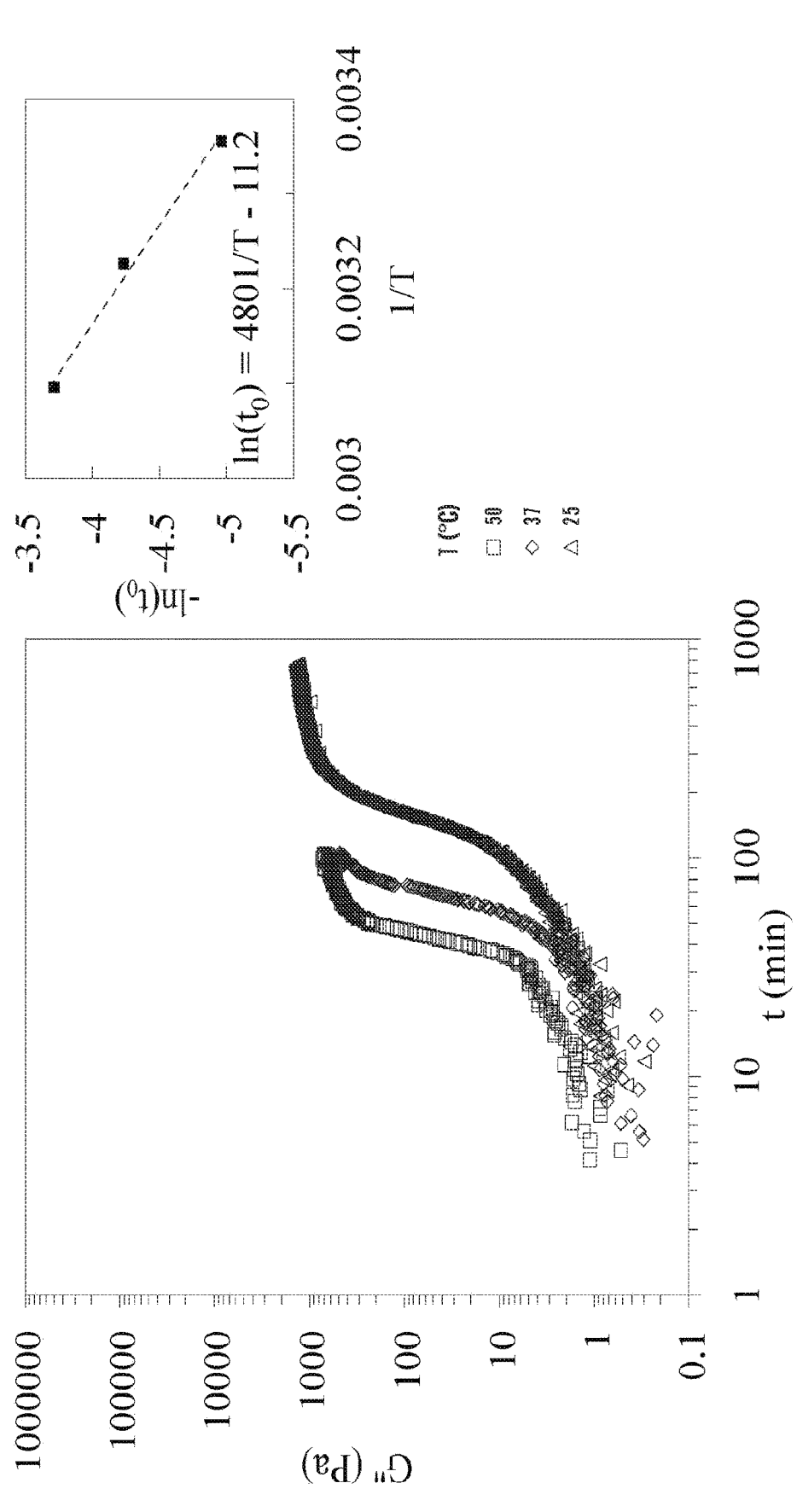
Figure 2E:
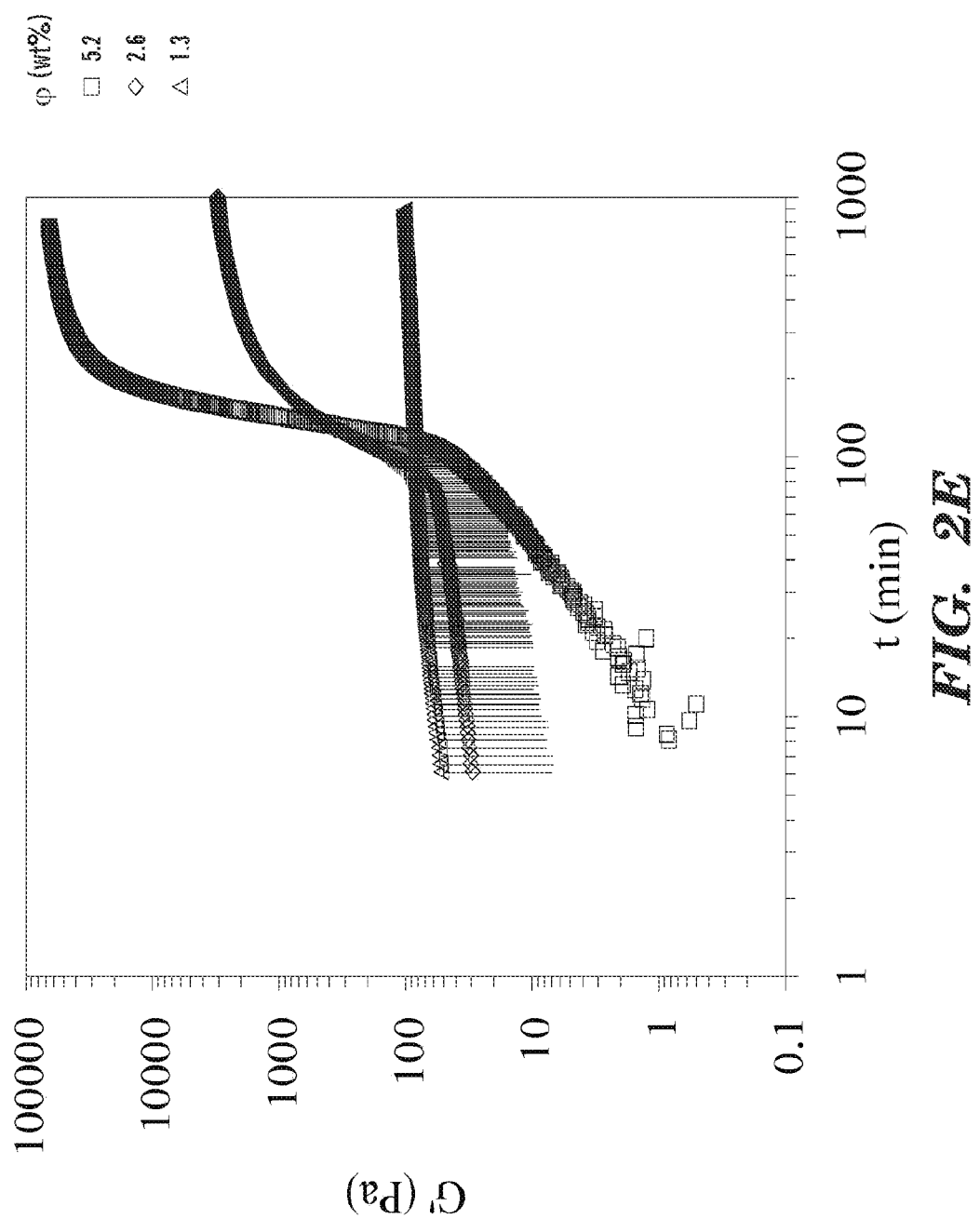
Figure 2F:
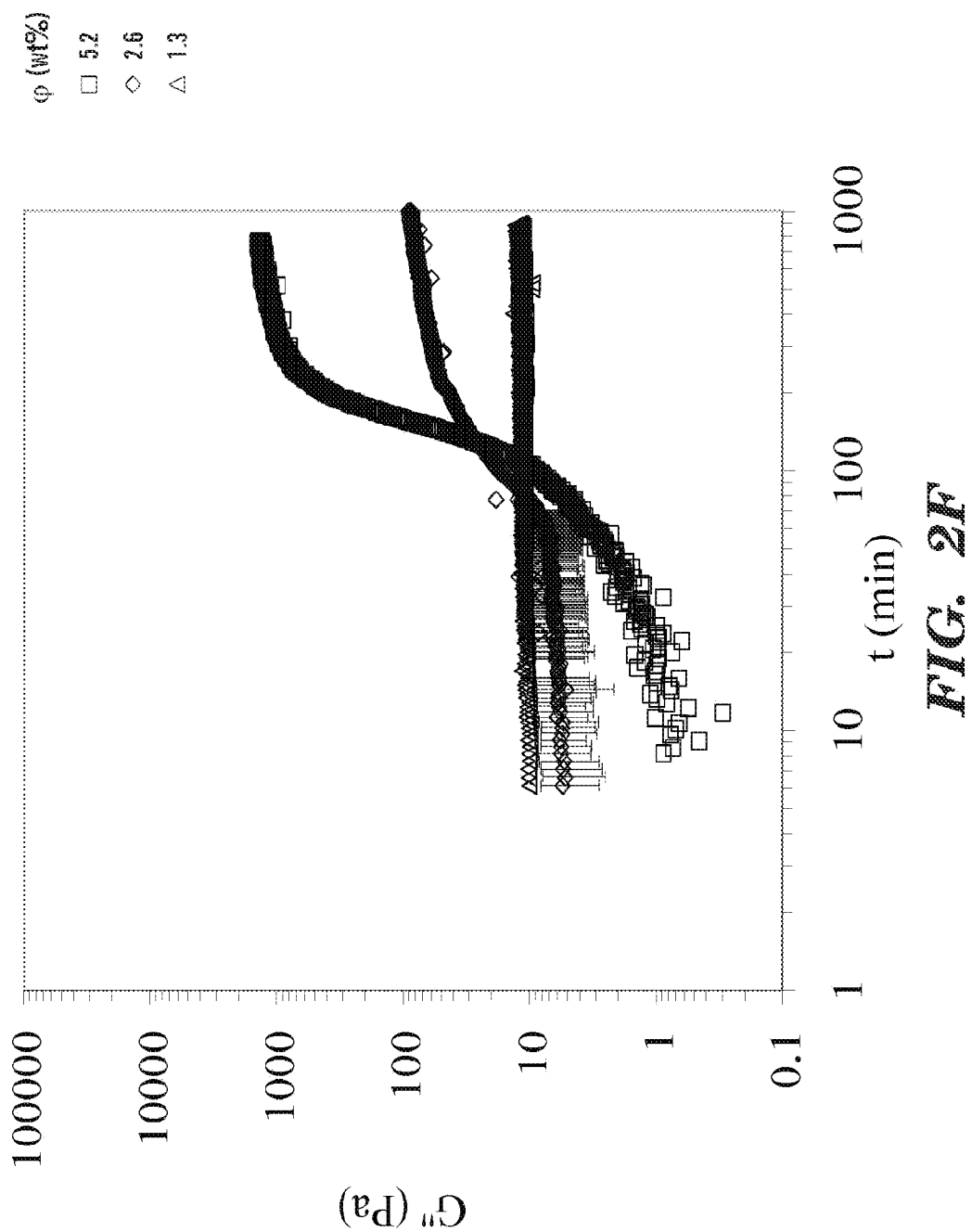

The present invention also provides for methods of controlling gelation time of silk fibroin initiated by vortexing a silk fibroin solution for a sufficient period of time to initiate gelation under conditions that gelation occurs within minutes to hours. Hydrogelation kinetics can be controlled easily by changing the processing parameters (FIGS. 2A-2F), such as vortex time (FIGS. 2A and 2B), post-vortex assembly temperature (FIGS. 2C and 2D), and silk concentration (FIGS. 2E and 2F). By controlling these parameters, self-assembly and hydrogelation kinetics of silk fibroin may be adjusted from using minutes to hours. This may bring many advantages to using silk fibroin hydrogels in biomedical applications, such as homogeneous encapsulation of cells in 3-D, namely, cells can be introduced immediately before the rapid gelation due to the apparent percolation transition to prevent cell sedimentation.

Additionally, understanding the hydrogelation kinetics of silk fibroin and controlling the parameters accordingly to control the gelation time may also help the homogeneous encapsulation of cells/active agents. For example, the shear storage modulus (G') values at the apparent percolation may be in a rather narrow range, for example, between 30 Pa and 100 Pa (at 10 rad/s) for many self-assembly conditions. Therefore, the solution viscoelastic properties of silk fibroin can be estimated accordingly and decisions can be made in terms of when the cells/active agents can be introduced to silk fibroin for homogeneous encapsulation.

As noted, the gelation time may be controlled by adjusting the time period of the vortex treatment. Adjusting the time period of the vortex treatment can effectively change the formation time of the silk gelation without significantly altering the final mechanical properties of the self-assembled silk hydrogels. For example, FIGS. 2A and 2B show the time evolution of the shear storage (G') and loss modulus (G"), respectively after vortexing the silk fibroin solutions for different times, $t_v$ (25° C., $\varphi$=5.2 wt %). There was a noted increase in the initial G' values immediately after vortexing with increasing vortex time, presumably due to increasing concentration of macromolecule clusters. Moreover, the apparent jump in G' attributed to increasing cluster connectivity shifted to shorter assembly times, i.e., $t_a^*$ decreases with increasing vortex time ($t_a^*$~35 min, 50 min, 100 min and >1000 min for $t_v$=11 min, 9 min, 7 min and 0 min, respectively). The increase in stiffness after $t_a^*$ was slower with increasing vortex time and the apparent equilibrium stiffness of the final hydrogel was essentially independent of the vortex time.

The gelation time may be controlled by the temperature of the silk fibroin solution after the vortex treatment. Within certain range of post-vortex temperature, hydrogelation kinetics of vortexed silk solutions increases by increasing the post-vortex assembly temperature. For example, FIGS. 2C and 2D show the time evolution of rheological properties at different post-vortex self-assembly temperatures of silk fibroin ($\varphi$=5.2 wt %, $t_v$=7 min). A master curve of the G' data shown in FIG. 2C could be constructed by normalizing the assembly time by a time shift factor, $t_0$, indicating that the self-assembly mechanism at different temperatures may be similar within the studied temperature range. As a further note, an Arrhenius type plot shows a linear dependence of the time shift factor as a function of reciprocal assembly temperature ($\ln(t_0)$=4801/T−11.2, shown as in the inset of FIG. 2D). A detailed analysis of the temperature dependence of the gelation time demonstrates that the logarithm of "substantial gelation time, $t_a^*$ (for G' ca. 100 Pa)" shows approximately linear dependence on reciprocal T, with $t_a^*$ (min)=exp(5403/T(K)−13.4) (for $t_v$=7 min and $\varphi$=5.2 wt %). For comparison, the time evolution of G' and G" for the non-vortexed solution at 50° C. were also given in FIG. 2A, which shows no detectable change in the viscoelastic behavior after 1,000 min, indicating the significant effect of vortexing on hydrogelation kinetics.

The gelation time may also be controlled by the concentration of the silk fibroin solution. The final hydrogel stiffness may be dependent on the initial protein concentration. For example, FIGS. 2E and 2F show the time evolution of the viscoelastic properties for different silk concentrations (25° C. for $t_v$=7 min). The initial G' values after vortexing apparently increased with decreasing silk concentration. This observation could be attributed to the increasing effect of vortex-induced concentration fluctuations and formation of a higher concentration of macromolecule clusters with decreasing protein concentration. At low protein concentrations (0.32<$\varphi$<1.3 wt %) G'~$\varphi^{1.5}$, while at higher protein concentrations (1<$\varphi$<5.2 wt %) G'~$\varphi^4$. The concentration dependence of network stiffness of vortexed silk hydrogels in the high concentration regime resembles that in shear-induced gelation of amphiphilic polymers in the entangled regime (G'~$\varphi^{3.7}$) (Cadix et al., 38 Macromol. 527-36 (2005)). A much weaker theoretical concentration dependence (G'~$\varphi^{2.5}$) was observed for highly crosslinked, semi-flexible biopolymer chain networks (Mackintosh et al., 75 Phys. Rev. Lett. 4425-28 (1995)).

In addition, various other factors may also affect the gelation time. For example, the rotational speed of vortexer. Those of ordinary skill in the art, in light of the present application, are able to alter the rotational speed of vortex treatment, to produce the desired level of gelation and the desired time frame in which gelation occurs. Further, vortex speed and sample volume may also affect the vortex time ($t_v$) dependence and silk concentration dependence of the gelation time.

The invention also relates to a method of embedding at least one active agent in silk fibroin gel. The method comprises, for example, vortexing a silk fibroin solution for a sufficient period of time to initiate gelation, introducing the agent(s) to the silk fibroin solution before substantial gelation occurs in the silk fibroin solution, and allowing the silk-fibroin gel to complete gelation to form a silk fibroin gel-embedded active agent.

The active agent can represent any material capable of being embedded in the silk fibroin gel. For example, the agent may be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, or combinations thereof. See, e.g., PCT/US09/44117; U.S. Patent Application Ser. No. 61/224,618). The agent may also be a combination of any of the above-mentioned agents. Encapsulating either a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See U.S. Patent Application Ser. No. 61/226,801.

When an agent is introduced into the silk fibroin solution after the vortex treatment, the conditions of the vortex treatment may be adjusted so that gelation occurs some period of time after the vortex treatment. If gelation occurs during the vortex treatment or immediately thereafter, an insufficient amount of time may exist to introduce the agent into the silk fibroin solution. For example, when the agent is introduced after the vortex treatment, the silk fibroin undergoes gelation at a time period ranging from about five minutes to about two hours after the vortex treatment.

When introducing therapeutic agents or biological material into the silk fibroin, other materials known in the art may also be added with the agent. For instance, it may be desirable to add materials to promote the growth of the agent (for biological materials), promote the functionality of the agent after it is released from the silk gel, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R. G. Landes Co., Austin, Tex., 1995). Additional options for delivery via the gels include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve gel-tissue interfaces; antimicrobial peptides; and proteins and related compounds.

Additional biocompatible material may also be blended into the silk fibroin hydrogels, such as polyethylene oxide (see, e.g., U.S. Patent Application Ser. No. 61/225,335), polyethylene glycol (see PCT/US09/64673), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, glycerol (see PCT/US2009/060135), and other biocompatible polymers, see WO 2004/0000915. Alternatively, the silk may be mixed with hydroxyapatite particles, see PCT/US08/82487. As noted herein, the silk fibroin may be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

The silk-fibroin embedded active agents or biological materials may be suitable for long term storage and stabilization of the cells and/or active agents. Cells and/or active agents, when incorporated in the silk hydrogel of the present invention, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk fibroin hydrogels without refrigeration. Importantly, temperature-sensitive bioactive agents can be delivered (e.g., through injection) into the body in silk hydrogels and maintain activity for a longer period of time than previously imagined. See, e.g., PCT/US2010/026190.

The silk-fibroin embedded active agents (e.g., therapeutic agents) or biological materials are suitable for a biodelivery device. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US07/020789; PCT/US08/55072; PCT/US09/44117. Some embodiments of the present invention relate to the utility of silk-fibroin embedded therapeutic agents or biological materials as drug delivery systems for potential utility in medical implants, tissue repairs and for medical device coatings.

The silk fibroin hydrogel structure enables the biodelivery vehicle to have a controlled release. Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the bioactive agent from the silk hydrogel may be designed to occur over time, for example, for greater than about 12 hours or 24 hours, inclusive; greater than 1 month or 2 months or 5 months, inclusive. The time of release may be selected, for example, to occur over a time period of about 12 hours to 24 hours, or about 12 hours to 1 week. In another embodiment, release may occur for example on the order of about 1 month to 2 months, inclusive. The controlled release time may be selected based on the condition treated. For example, a particular release profile may be more effective where consistent release and high local dosage are desired.

A pharmaceutical formulation may be prepared that contains the silk fibroin hydrogel having encapsulated bioactive agents. The formulation can be administered to a patient in need of the particular active agent that has been encapsulated in the silk fibroin. The pharmaceutical formulation may be administered by a variety of routes known in the art including topical, oral, ocular, nasal, transdermal or parenteral (including intravenous, intraperitoneal, intramuscular and subcutaneous injection as well as intranasal or inhalation administration), and implantation. The delivery may be systemic, regional, or local. Additionally, the delivery may be intrathecal, e.g., for delivery to the central nervous system.

When desired, the active agent-containing silk hydrogel may include a targeting ligand or precursor targeting ligand. Targeting ligand refers to any material or substance which may promote targeting of the pharmaceutical formulation to tissues and/or receptors in vivo and/or in vitro with the formulations of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and iodo acetyl groups.

In preparation for in vivo application, the silk fibroin of the present invention may be formulated to include excipients. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations may also include bulking agents, chelating agents, and antioxidants. Where parenteral formulations are used, the formulation may additionally or alternately include sugars, amino acids, or electrolytes.

More specifically, examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See, e.g., U.S. Pat. No. 5,589,167. Exemplary surfactants include nonionic surfactants, such as Tween surfactants, polysorbates, such as polysorbate 20 or 80, etc., and the poloxamers, such as poloxamer 184 or 188, pluronic polyols, and other ethylene/ polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator or ordinary skill.

The present invention also provides for a method of preparing reversible shear-thinning silk fibroin gels. The method comprises vortexing a silk fibroin solution for a sufficient period of time to initiate gelation of the silk fibroin. The silk fibroin then undergoes substantial gelation after the vortex treatment thereby forming a reversible shear-thinning silk fibroin gel. An important practical consideration for encapsulation/delivery application of hydrogel/bioactive molecules scaffolds is the ease of application into the target cite not only with high temporal precision by also with high spatial precision. For example, a shear-thinning hydrogel material can be implanted with minimal invasion to the delivery site, such as by injection through a needle. A hydrogel that shear-thins into a sol during injection may enable more homogeneous delivery of active agent and/or cells (e.g., to the wound site) as compared with cell delivery in solution. In addition, it is advantageous for the shear-thinned hydrogel material to recover quickly, even immediately, to form a stiff network after removal of applied shear force, facilitating localization of a uniform density of cells and/or active agent at the delivery site.

Figure 3A:
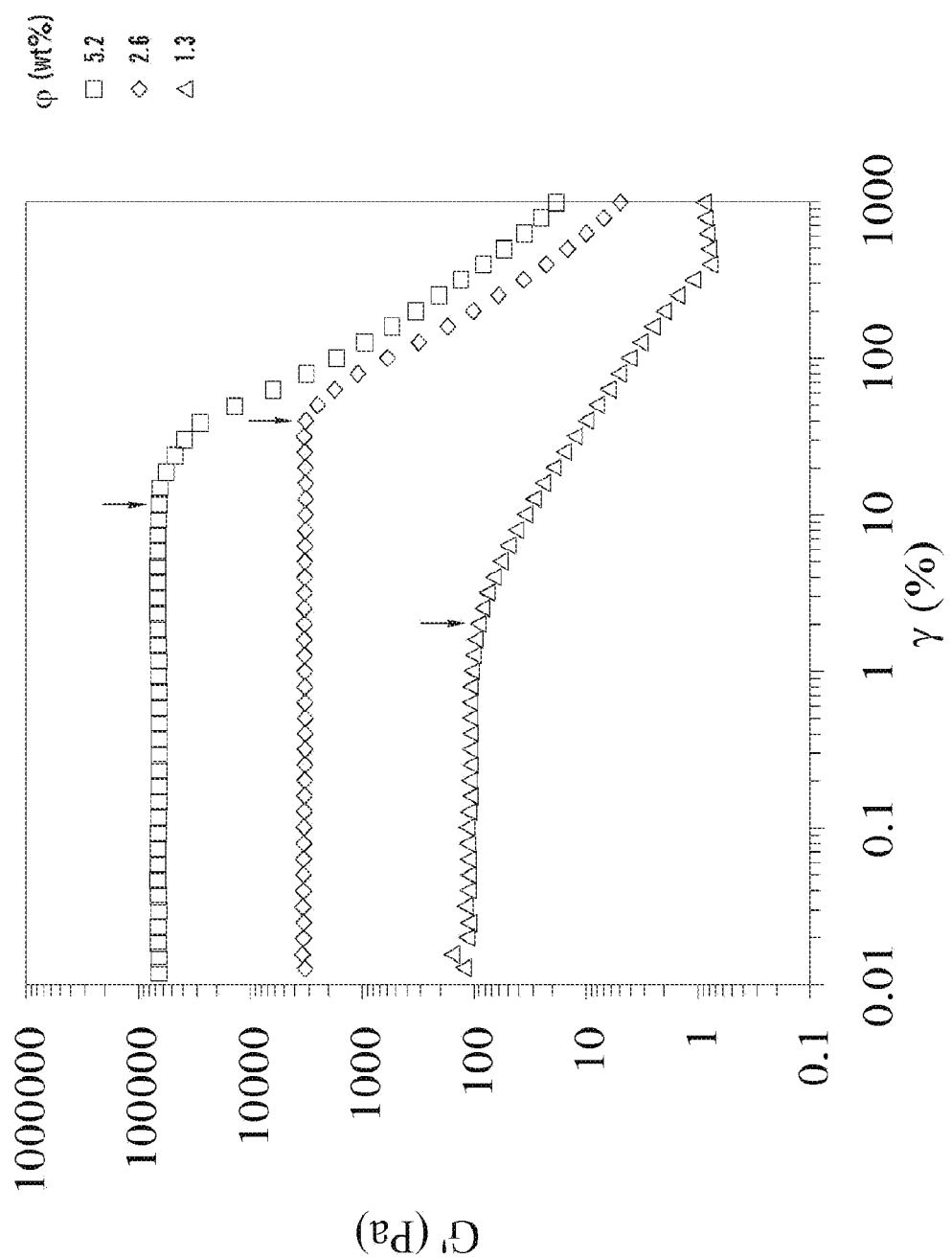
FIGS. 3A and 3B depict strain sweeps collected from vortex-induced hydrogels with different silk concentrations (arrows show apparent yielding).
Figure 3B:
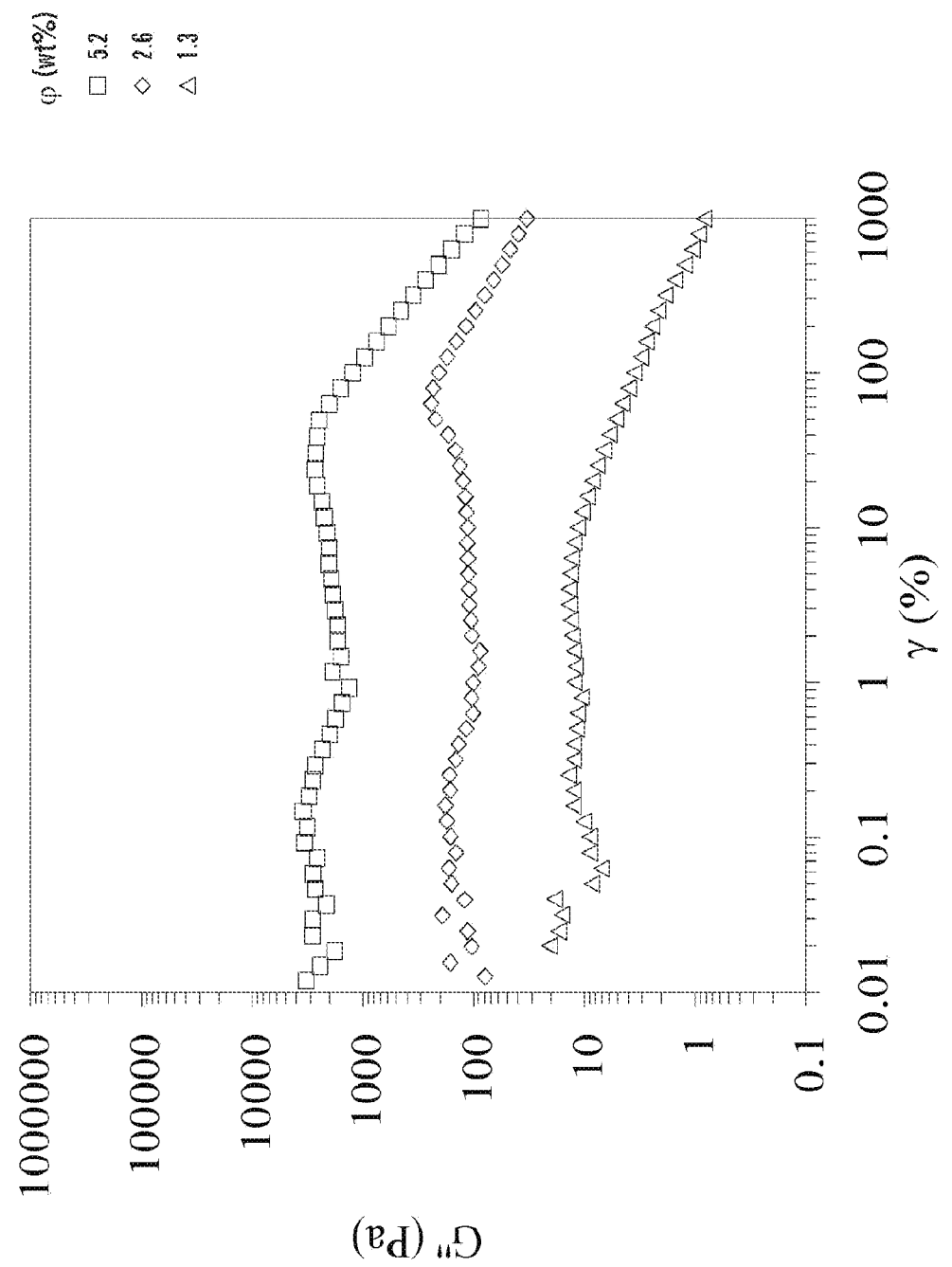

Thus, the silk fibroin gels prepared by the vortex treatment of the present invention may be shear-thinned. In one embodiment, the shear-thinning behavior of vortex-induced hydrogels formed on the rheometer plate has been examined. FIGS. 3A and 3B show the dependence of G' and G" on the amplitude of the applied shear force as a function of protein concentration. Hydrogels display a linear viscoelastic regime and apparently yield above the shear amplitude, $\gamma_B$ ($\gamma_B$~2%, ~40% and ~10% for 1.3 wt %, 2.6 wt % and 5.2 wt % hydrogels, respectively) followed by apparent shear thinning. Shear thinning could be attributed to the rupture of dangling chain entanglement crosslinks and the breaking apart of clusters from the hydrogel network at high shear amplitude. From a practical viewpoint, shear thinning of the hydrogel (e.g., during injection to an in vivo site) could enable a more homogeneous delivery of cells and/or active agents in the shear-thinned sol to the wound site as compared with cells/active molecules delivery in solution. The apparent decrease in $\gamma_B$ from 2.6 wt % to 5.2 wt % may be due to formation of a slip layer at the hydrogel/rheometer plate interface at high shear for very stiff hydrogels leading to an underestimation of $\gamma_B$.

Figure 3C:
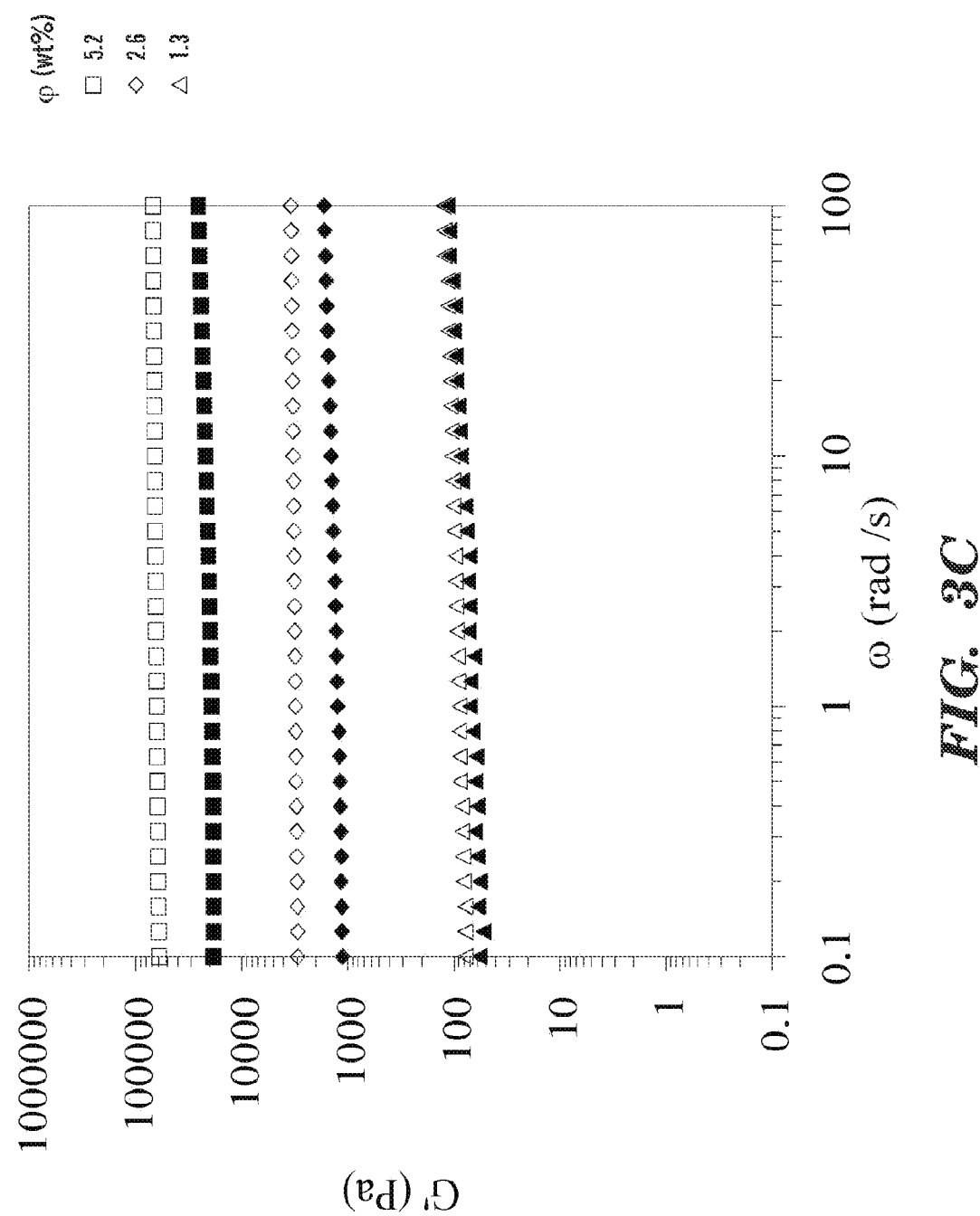
Figure 4:
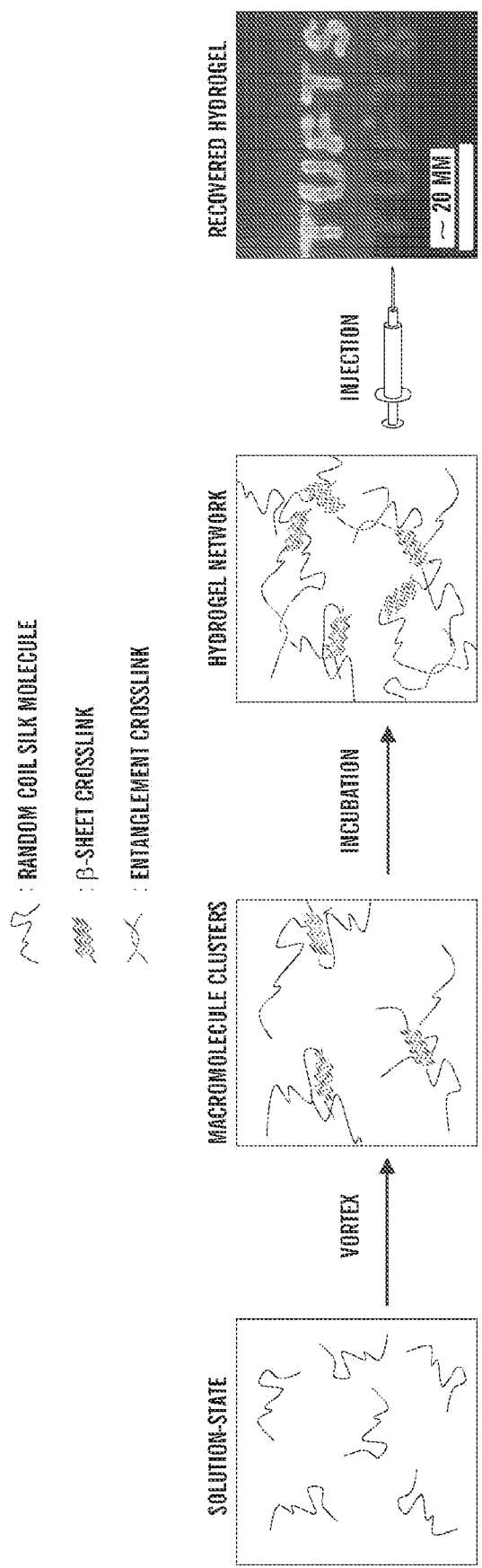
FIG. 4 is a scheme depicting the possible mechanism of silk fibroin hydrogelation and the resulting injectable silk hydrogels.

The stiffness of vortex-induced silk fibroin gels of the invention may recover from shear-thinning after removal of applied shear. For example, the recovery of crosslinks in vortexed hydrogels after shear-thinning may be examined by comparing frequency sweeps collected before and immediately after directly injecting the gels through a 21 gauge needle onto the rheometer plate (FIGS. 3C and 3D). Injection through a needle was chosen to demonstrate the possibility of injection of the hydrogels in a minimally invasive manner to a delivery site. For all hydrogels, there was significant recovery of stiffness immediately after injection (for $\varphi$=1.3 wt %, G' recovered almost to the pre-injection value, while for higher protein concentrations G'~⅓ of the pre-injection value). All hydrogels essentially displayed frequency independent shear modulus immediately after cessation of applied shear due to injection. It is unlikely that the shear-recovery of vortexed hydrogels after shear thinning is due to the disruption and reformation of permanent, intermolecular β-sheet crosslinks. Therefore, the presence of another crosslinking mechanism in addition to the intermolecular β-sheet crosslinks could be hypothesized similar to that proposed for 3-hairpin peptide hydrogels (Haines-Butterick et al., 2007; Yucel et al., 2008; Yucel, Ph.D. Dissertation, 2008). For example, large, β-sheet rich clusters could slide past each other during shear thinning by the temporary release of intercluster, dangling chain entanglements at high shear amplitudes, which may reform permanently after removal of shear, with no significant change in the overall β-sheet content. Overall, considering the high stiffness values and the frequency independence of viscoelastic properties immediately after injection, these materials may be used to facilitate localization of cells at the injection site with high spatial precision.

The present invention also provides methods of delivering a reversibly shear-thinned silk fibroin gel to a target site. The method comprises vortexing a silk fibroin solution for a sufficient period of time to initiate gelation, allowing substantial gelation to occur after the vortex treatment to form a silk fibroin gel, introducing the silk fibroin gel through a shear-inducing delivery device to the target site while applying a shear force to shear-thin the silk fibroin gel, and removing the shear force, whereupon the shear-thinned silk fibroin gel recovers from shear-thinning and re-gels. In one embodiment, such reversibly shear-thinned silk fibroin gel is delivered locally to the target site with high spatial precision. The delivery devices may be any delivery devices known in the art that can produce shear force to the hydrogels. In another embodiment, the reversibly shear-thinned silk fibroin gel is delivered locally to the target site by injection through a needle.

Another embodiment of the invention relates to a method of encapsulating or embedding bioactive agents to a reversible shear-thinned silk fibroin gel, and delivering the reversibly shear-thinned silk fibroin gel-encapsulated/embedded active agent to a target site. Such method may be used for homogeneous delivery of one or more active agents to a target site. The method comprises vortexing a silk fibroin solution for a sufficient period of time to initiate gelation, introducing at least one bioactive agent to the silk fibroin solution before substantial gelation occurs in the silk fibroin solution, thereby forming a silk fibroin gel-embedded active agent that may be shear-thinned reversibly, introducing to the target site the active agent-encapsulated silk fibroin gel through a shear-inducing delivery device to the target site while applying a shear force to shear-thin the silk gel-embedded bioagent, and removing the shear force, whereupon the shear-thinned silk fibroin gel-embedded bioagent recovers gel form. The method hence may distribute the active agent contained in the silk gel at the target site homogeneously.

The novel techniques based on vortexing to induce silk fibroin gelation, described herein, form silk fibroin gels, and also control the rate of β-sheet formation and the concomitant hydrogelation kinetics of aqueous silk fibroin solutions. Shear gradient-induced changes in silk fibroin structure and solution viscoelastic properties post-vortex treatment are presented herein. The novel technique controls the post-shear self-assembly and hydrogelation kinetics of silk fibroin for cell encapsulation and delivery applications. The silk fibroin gels may be characterized by various techniques. CD spectroscopy indicates that vortexing aqueous solutions of silk leads to a transition from an overall protein structure that is initially rich in random coil to protein structure that is rich in β-sheet content. Dynamic oscillatory rheology experiments collected under the same assembly conditions as the CD experiments indicate that the increase in β-sheet content due to intramolecular conformational changes and intermolecular self-assembly of the silk fibroin is directly correlated with the subsequent changes in viscoelastic properties due to hydrogelation. Vortexing low-viscosity silk solutions leads to orders of increase in the complex shear modulus, G* and formation of rigid hydrogels (G*~70 kPa for 5.2 wt % protein concentration). The vortex-induced, β-sheet-rich silk hydrogels consist of permanent, physical, intermolecular crosslinks, although the sol-gel may be reversibly manipulated by shear stress. The novel vortexing technique is simple, yet versatile. The hydrogelation kinetics can be controlled easily (from minutes to hours) by changing the vortex time, assembly temperature and/or protein concentration, providing a useful timeframe for cell encapsulation. The shear thinning and recovery behavior of vortex-induced silk hydrogels are studied using rheology to highlight the suitability of these materials as versatile cell delivery scaffolds. Vortex-induced hydrogels may be shear-thinned by injection through needles, and the hydrogel stiffness recovered immediately after removal of applied shear. Physicochemical characterization can be further correlated with cell behavior to study the applicability of these materials for homogeneous 3D cell encapsulation, homogeneous delivery in vivo, and localization of hydrogel/cell scaffolds at the injection site.

The invention will be further characterized by the following examples which are intended to be exemplary of the embodiments.

The present invention can be defined in any of the following numbered paragraphs:

A method of forming silk fibroin gel, comprising vortexing a silk fibroin solution for a sufficient period of time to initiate intermolecular self-assembly of silk fibroin β-sheet structure, wherein substantial silk fibroin gelation occurs in less than about 16 hours after the vortexing.

The method of paragraph 75, wherein said vortexing yields a solid phase and an aqueous phase, and wherein the method further comprises removing said solid phase and allowing gelation of the aqueous phase.

The method of paragraph 75 or 76, wherein the silk fibroin in the solution has a concentration about 6 wt % or lower.

The method of paragraph 77, wherein the silk fibroin in the solution has a concentration ranging from about 1.0 wt % to about 5.2 wt %.

A method of controlling gelation time of silk fibroin initiated by vortexing a silk fibroin solution for a sufficient period of time to initiate gelation, wherein the gelation time is controlled by adjusting one or more of (a) the time period of the vortex treatment; (b) the concentration of the silk fibroin in solution; or (c) the temperature of the silk fibroin solution after the vortex treatment.

A method of preparing a reversible shear-thinning silk fibroin gel, comprising vortexing a silk fibroin solution for a sufficient period of time to initiate gelation, wherein the silk fibroin undergoes substantial gelation after the vortex treatment thereby forming a reversibly shear-thinning silk fibroin gel.

A method of preparing a silk fibroin gel-encapsulated active agent, comprising:

vortexing a silk fibroin solution for a sufficient period of time to initiate gelation; introducing at least one active agent to the silk fibroin solution before substantial gelation occurs in the silk fibroin solution;

allowing the silk-fibroin to gel, forming a silk fibroin gel-encapsulated active agent.

The method of paragraph 81, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

The method of paragraph 81, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.

The method of paragraph 83, the active agent further comprises a cell growth media.

The method of paragraph 81, wherein the silk fibroin gel-encapsulated active agent is suitable for a biodelivery device.

The method of paragraph 81, wherein the silk fibroin gel-encapsulated active agent is suitable for a medical implant or a tissue repair material.

A method of delivering a reversibly shear-thinned silk fibroin gel to a target site, comprising:

vortexing a silk fibroin solution for a sufficient period of time to initiate gelation, wherein the silk fibroin undergoes substantial gelation after the vortex treatment to form a silk fibroin gel;

introducing the silk fibroin gel through a shear-inducing delivery device to the target site while applying a shear force to shear-thin the silk fibroin gel; and removing the shear force, whereupon the shear-thinned silk fibroin gel recovers from shear-thinning and re-gels.

The method of paragraph 87, further comprising adding an active agent to said silk fibroin solution.

The method of paragraph 87 or paragraph 88 wherein said reversible shear-thinning silk fibroin gel is delivered locally to said target site with high spatial precision.

The method of paragraph 89, wherein said reversible shear-thinning silk fibroin gel is delivered locally to said target site by injection through a needle.

The method of paragraph 89, wherein the method is suitable for implanting a medical implant or a tissue repair material.

A method for homogeneous delivery of at least one active agent to a target site, comprising:

vortexing a silk fibroin solution for a sufficient period of time to initiate gelation;

introducing at least one active agent to the silk fibroin solution either before vortexing or before substantial gelation occurs in the silk fibroin solution, thereby forming a silk fibroin gel-encapsulated active agent that may be shear-thinned reversibly;

introducing to the target site the active agent-encapsulated silk fibroin gel through a shear-inducing delivery device to the target site while applying a shear force to shear-thin the agent-encapsulated silk fibroin gel; and removing the shear force, whereupon the shear-thinned silk fibroin gel-encapsulated agent recovers gel form, thereby distributing the active agent in the gel form at the target site homogeneously.

The method of paragraph 92, wherein said reversible shear-thinning silk fibroin gel is delivered locally to said target site with high spatial precision.

The method of paragraph 93, wherein said reversible shear-thinning silk fibroin gel is delivered locally to said target site by injection.

The method of paragraph 92, wherein the at least one silk fibroin gel-encapsulated active agent is delivered to the target site in vivo.

A method of preparing a silk fibroin gel-encapsulated active agent, comprising:

introducing at least one active agent to a silk fibroin solution; and vortexing the silk fibroin solution for a sufficient period of time to initiate gelation.

The method of paragraph 96, further comprising adding a cell population to said vortexed solution before significant onset of gelation.

The method of paragraph 96 or paragraph 97, further comprising reversibly shear-thinning the gel by passing it through a hypodermic needle.

A silk fibroin gel-encapsulated active agent prepared by the method of any one of paragraph 96 to paragraph 98.

EXAMPLES

Example 1. Preparation of Aqueous Silk Fibroin Solutions

Silk fibroin aqueous solutions were prepared as previously described in the literature. See Sofia et al., 54 J. Biomed. Mater. Res. 139-48 (2001). Briefly, *Bombyx mori* cocoons were boiled for 40 min in an aqueous solution of 0.02 M $NaC_{O3}$ and then rinsed thoroughly with deionized water. After overnight drying, the extracted silk fibroin was dissolved in an aqueous solution of 9.3 M LiBr at 60° C. overnight. The resulting solution was dialyzed against deionized water using Slide-A-Lyzer dialysis cassettes (MWCO 3,500, Pierce, Thermo Scientific, Waltham, Mass.) for two days to remove the residual salt. The final concentration of the silk fibroin was approximately 5.3 wt %. Lower concentration silk solutions were prepared by diluting the 5.3 wt % stock solution with deionized water. Additionally, the silk fibroin solution may be concentrated, for example, to about 30% (w/v). Briefly, the silk fibroin solution with a lower concentration may be dialyzed against a hygroscopic polymer, such as PEG, amylose or sericin, for a time period sufficient to result in a desired concentration. See, e.g., WO2005/012606.

The silk fibroin solution can be combined with one or more biocompatible polymers such as polyethylene oxide, polyethylene glycol, collagen, fibronectin, keratin, polyaspartic acid, polylysin, alginate, chitosan, chitin, hyaluronic acid, and the like; or one or more active agents, such as cells, enzymes, proteins, nucleic acids, antibodies and the like, as described herein. See, e.g., WO2004/062697 and WO2005/012606. Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; U.S. Application Ser. No. 61/227,254; Ser. No. 61/224,618; Ser. No. 12/192,588.

Example 2. Vortex-Induced Hydrogelation

A 1 ml aliquot of silk solution was equilibrated at 25° C. in a vial kept in a water bath for 10 min and mixed for predetermined times at 3,200 rpm using a vortexer (Fisher Scientific, Pittsburgh, Pa.) to induce silk self-assembly and hydrogelation. Such prepared silk hydrogelation was characterized by CD and rheology experiment. Increasing the vortex time increased the solution turbidity and eventually bulk phase separation of a white and solid-like material was observed, especially at lower protein concentrations. Both CD and rheology data were collected from turbid solutions after removal of the solid phase.

Example 3. Circular Dichroism Spectroscopy

Circular dichroism (CD) spectra were collected using an Aviv Model 410 CD spectrometer (Aviv Biomedical, Inc., Lakewood, N.J.). After vortexing, aqueous silk solutions were immediately loaded in a 0.1 mm quartz cell within a temperature controlled cell holder. CD wavelength scans between 210 nm and 260 nm or time sweeps at 216 nm were collected at 25° C. Due to the high silk concentrations, the high dynode voltages below 210 nm lead to erroneous data. The CD spectrum of water collected immediately before each measurement was used for background correction.

The mean residual ellipticity was calculated from $$[\theta] = \frac{\theta \cdot M}{10 \cdot c \cdot l \cdot n}\left(\frac{\deg \cdot cm^2}{dmol}\right)$$

where θ is the measured ellipticity (deg), M is the mean molecular mass (g/mol), c is the protein concentration (g/cm³), l is the path length (cm), and n is the number of residues. M and n for *B. mori* heavy chain were taken as 391,563 g/mol and 5263, respectively (Zhou et al, 28 Nucleic Acids Res. 2413-19 (2000)). For protein concentration measurements, a 0.5 mL aliquot of silk solution was dried at 60° C. overnight and the solution concentration was calculated from the weight of the dried film.

Example 4. Dynamic Oscillatory Rheology

Dynamic oscillatory time, frequency and strain sweeps were performed using an ARES strain-controlled rheometer (TA Instruments, New Castle, Del.) with 25 mm or 50 mm diameter stainless steel parallel plate geometries at 0.5 mm measuring gap distance. In a typical experiment, the silk solution was applied slowly via a syringe on the rheometer plate to prevent shearing of the sample immediately after vortexing. The normal force applied on the sample during lowering of the top plate was limited to 0.1 N. A low viscosity mineral oil and the solvent trap supplied by TA instruments were used to prevent sample evaporation from the sides of the plate. Dynamic oscillatory time sweeps were collected at a low strain amplitude (γ=1%, =10 rad/s) to prevent possible sample manipulation due to applied shear during measurements. Frequency sweeps were collected over a wide frequency range ($\gamma=1\%$, $\omega=0.1$-$100$ rad/s) after each time sweep. To observe the time evolution of the frequency dependence of viscoelastic properties, frequency sweeps were collected continuously over a narrower range ($\gamma=1\%$, $\omega=0.5$-$100$ rad/s). At the applied shear amplitude, continuous collection of frequency sweeps had no detectable effect on the measured rheological properties. Strain sweep measurements were performed from $\gamma=0.01$-$1000\%$ ($\omega=10$ rad/s) at the end of each experiment to determine the linear viscoelastic regime of the final hydrogel.

Example 5. Injection Studies

To study the injectability of vortexed hydrogels and the shear-recovery behavior, vortexed silk solutions were either loaded into 1 ml syringes immediately after vortexing and allowed to gel overnight or loaded into syringes after overnight hydrogelation in vials. A 21 gauge needle was connected to the syringe and the hydrogel was injected through the needle directly onto the rheometer plate. A frequency sweep was collected over a wide frequency range ($\gamma=1\%$, $\omega=0.1$-$100$ rad/s) within 10 min of injection of the sample.

The invention claimed is:

1. A method of preparing a reversible shear-thinning silk fibroin gel, comprising:
    vortexing a silk fibroin solution for a sufficient period of time to initiate gelation, wherein the silk fibroin undergoes gelation after the vortex treatment thereby forming a reversibly shear-thinning silk fibroin gel, wherein concentration of silk fibroin in the solution is between about 1 wt % and about 6 wt %; and
    removing a solid phase from the silk fibroin solution, wherein the solid phase results from the vortexing step.

2. The method of claim 1, further comprising introducing at least one active agent to the silk fibroin solution either before vortexing or before substantial gelation occurs in the silk fibroin solution, thereby forming a silk fibroin gel-encapsulated active agent that may be shear-thinned reversibly.

3. The method of claim 1, wherein the silk fibroin gel-encapsulated active agent is delivered to a target site in vivo.

4. The method of claim 1, further comprising adding a cell population to the vortexed silk fibroin solution before initiation of gelation.

5. The method of claim 1, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

6. The method of claim 1, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.

7. The method of claim 1, wherein the concentration of silk fibroin in the solution ranges from about 1 wt % fibroin to about 5.2 wt % fibroin.

8. The method of claim 1, wherein the silk fibroin solution is vortexed for at least two separate sections of time.

9. The method of claim 1, wherein the shear storage modulus of the reversibly shear-thinning silk fibroin gel is at least 100 Pa.

* * * * *